(12) United States Patent
Miyake et al.

(10) Patent No.: US 11,591,577 B2
(45) Date of Patent: *Feb. 28, 2023

(54) METHOD FOR PRODUCING HYDROXY-L-PIPECOLIC ACID

(71) Applicant: API CORPORATION, Tokyo (JP)

(72) Inventors: Ryoma Miyake, Tokyo (JP); Hiroshi Kawabata, Tokyo (JP)

(73) Assignee: API CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/177,823

(22) Filed: Feb. 17, 2021

(65) Prior Publication Data

US 2021/0180097 A1 Jun. 17, 2021

Related U.S. Application Data

(62) Division of application No. 15/765,148, filed as application No. PCT/JP2016/079123 on Sep. 30, 2016, now Pat. No. 10,954,539.

(30) Foreign Application Priority Data

Oct. 2, 2015 (JP) ................................. 2015-197231

(51) Int. Cl.
| | | |
|---|---|---|
| *C12N 9/02* | (2006.01) | |
| *C12P 17/12* | (2006.01) | |
| *C12N 9/10* | (2006.01) | |
| *C12N 9/06* | (2006.01) | |
| *C12N 15/09* | (2006.01) | |

(52) U.S. Cl.
CPC ......... *C12N 9/0071* (2013.01); *C12N 9/0016* (2013.01); *C12N 9/0022* (2013.01); *C12N 9/1096* (2013.01); *C12P 17/12* (2013.01); *C12Y 114/11028* (2013.01); *C12N 15/09* (2013.01)

(58) Field of Classification Search
CPC ............................... C12N 9/0071; C12P 17/12
See application file for complete search history.

(56) References Cited

U.S. PATENT DOCUMENTS

| | | |
|---|---|---|
| 2003/0199541 A1 | 10/2003 | Lampilas et al. |
| 2006/0205045 A1 | 9/2006 | Esaki et al. |
| 2010/0056566 A1 | 3/2010 | Plettenburg et al. |
| 2015/0211035 A1 | 7/2015 | Fujii et al. |
| 2015/0259715 A1 | 9/2015 | Kino et al. |
| 2016/0348081 A1 | 12/2016 | Hibi et al. |
| 2017/0306367 A1 | 10/2017 | Miyake et al. |
| 2018/0273993 A1 | 9/2018 | Miyake et al. |

FOREIGN PATENT DOCUMENTS

| | | |
|---|---|---|
| CN | 107109446 A | 8/2017 |
| WO | 2014/129459 A1 | 8/2014 |
| WO | 2015/115398 A1 | 8/2015 |
| WO | 2016/076159 A1 | 5/2016 |

OTHER PUBLICATIONS

Office Action issued in JP Patent Application No. 2017-543644, dated Nov. 10, 2020, along with a machine English-language translation.
Fujii et al., "Increase in the Rate of L-Pipecolic Acid Production Using lat-Expressing *Escherichia coli* by lysP and yeiE Amplification", *Biosci. Biotechnol. Biochem*, vol. 66, No. 9, pp. 1981-1984, 2002.
Byun et al., "Optimized Conversion of L-Lysine to L-Pipecolic Acid Using Recombinant Lysine Cyclodeaminase from *Streptomyces pristinaespiralis*", Biotechnology and Bioprocess Engineering, vol. 20, pp. 73-78, 2015.
Partial Supplementary European Search Report issued in EP Patent Application No. 16851899.1, dated Jul. 10, 2018.
Gillard et al., "Preparation of (2S,4R)-4-Hydroxypipecolic Acid and Derivatives" *J. Org. Chem.*, vol. 61, pp. 2226-2231, 1996.
International Search Report issued in PCT/JP2016/079123, dated Dec. 27, 2016.
International Preliminary Report on Patentability issued in PCT/JP2016/079123, dated Apr. 12, 2018.
1993 Sigma catalog entry P2519 for L-pipecolic acid p. 810 (Year: 1993).
Office Action issued in CN Patent Application No. 201680022697.X, dated Feb. 19, 2021, along with a machine English language translation.
Office Action issued in CN Patent Application No. 201680022697.X, dated Apr. 14, 2022, along with a machine English language translation.

*Primary Examiner* — Yong D Pak
(74) *Attorney, Agent, or Firm* — Greenblum & Bernstein, P.L.C.

(57) ABSTRACT

A novel method of producing high-purity hydroxy-L-pipecolic acids in an efficient and inexpensive manner while suppressing the production of hydroxy-L-proline is provided. The method includes allowing an L-pipecolic acid hydroxylase, a microorganism or cell having the ability to produce the enzyme, a processed product of the microorganism or cell, and/or a culture liquid comprising the enzyme and obtained by culturing the microorganism or cell, to act on L-pipecolic acid as a substrate in the presence of 2-oxoglutaric acid and ferrous ion, wherein the L-pipecolic acid hydroxylase has the properties:
(1) the enzyme can act on L-pipecolic acid in the presence of 2-oxoglutaric acid and ferrous ion to add a hydroxy group to the carbon atom at positions 3, 4, and/or 5 of L-pipecolic acid; and
(2) the enzyme has a catalytic efficiency (kcat/Km) with L-proline that is equal to or less than 7 times the catalytic efficiency (kcat/Km) with L-pipecolic acid.

12 Claims, 3 Drawing Sheets
Specification includes a Sequence Listing.

SEQUENCE LISTING

<160> NUMBER OF SEQ ID NOS: 40

<210> SEQ ID NO 1
<211> LENGTH: 858
<212> TYPE: DNA

<213> ORGANISM: Artificial Sequence
<220> FEATURE:
<223> OTHER INFORMATION: synthetic DNA

<400> SEQUENCE: 1

```
atgagaacgc attttgtggg tgaagttgca ttggacctgg cacgtctgga ggctgatctg      60
gcaacctgtc gtagcctgga gtggagcgaa gcgtattcgg attacgtctt tggtggtagc     120
tggaaaagct gcatgctgtg ggcgcctggt ggcgatgccg cgatggtgt tgtgacggac      180
tacgcgtacg accgtagcgc gggttttacg ccgcacgcag agcgcctgcc gtatctggca     240
gagcttattc gtgagactgc agatctggat cgcctgaatt tcgcgcgctt ggcgctggta     300
accaactctg tgattatccc gcaccgtgac ctgttggaat aagcgactt gccggacgaa      360
gctcgcaatg aacaccgtat gcacattccg ctggcgacca atgataactg cttcttcaac     420
gaggacaacg ttgtgtatcg tatgcgtcgt ggtgaagttt ggtttctgga tgccagccgt     480
attcatagcg tcgctgtcct gacggcgcag ccacgtatcc atctgatgct ggatttcgtg     540
gacaccccgg gtgcgggcag cttcacgcgc gttgcgggtg gcggcgttga ggccggcatc     600
ccggtcgatc gcatcgtgac ccgtccgccg ctgggcgacg acgagcgtgc ggacctgttc     660
ggtgtcgccc cactcctgtc catggatacc ttcgacgaag tgttttccat tgttatcaag     720
aaacacttcc gtcgtgatgg tggcagcgac tttgtgtggg acaccatgct ggaactggcg     780
gcgaagtctc cggatccggc cgtcctgccg cataccgaag aactgcgcaa gcactacacc     840
ctggaccgca gcgcataa                                                   858
```

<210> SEQ ID NO 2
<211> LENGTH: 285
<212> TYPE: PRT
<213> ORGANISM: Micromonospora chokoriensis

<400> SEQUENCE: 2

```
Met Arg Thr His Phe Val Gly Glu Val Ala Leu Asp Leu Ala Arg Leu
1               5                  10                  15

Glu Ala Asp Leu Ala Thr Cys Arg Ser Leu Glu Trp Ser Glu Ala Tyr
            20                  25                  30

Ser Asp Tyr Val Phe Gly Gly Ser Trp Lys Ser Cys Met Leu Trp Ala
        35                  40                  45

Pro Gly Gly Asp Ala Gly Asp Gly Val Val Thr Asp Tyr Ala Tyr Asp
    50                  55                  60

Arg Ser Ala Gly Phe Thr Pro His Ala Glu Arg Leu Pro Tyr Leu Ala
65                  70                  75                  80

Glu Leu Ile Arg Glu Thr Ala Asp Leu Asp Arg Leu Asn Phe Ala Arg
                85                  90                  95

Leu Ala Leu Val Thr Asn Ser Val Ile Ile Pro His Arg Asp Leu Leu
            100                 105                 110

Glu Leu Ser Asp Leu Pro Asp Glu Ala Arg Asn Glu His Arg Met His
        115                 120                 125

Ile Pro Leu Ala Thr Asn Asp Asn Cys Phe Phe Asn Glu Asp Asn Val
    130                 135                 140

Val Tyr Arg Met Arg Arg Gly Glu Val Trp Phe Leu Asp Ala Ser Arg
145                 150                 155                 160

Ile His Ser Val Ala Val Leu Thr Ala Gln Pro Arg Ile His Leu Met
                165                 170                 175

Leu Asp Phe Val Asp Thr Pro Gly Ala Gly Ser Phe Thr Arg Val Ala
            180                 185                 190
```

Gly Gly Gly Val Glu Ala Gly Ile Pro Val Asp Arg Ile Val Thr Arg
        195                 200                 205

Pro Pro Leu Gly Asp Asp Glu Arg Ala Asp Leu Phe Gly Val Ala Pro
    210                 215                 220

Leu Leu Ser Met Asp Thr Phe Asp Glu Val Phe Ser Ile Val Ile Lys
225                 230                 235                 240

Lys His Phe Arg Arg Asp Gly Gly Ser Asp Phe Val Trp Asp Thr Met
                245                 250                 255

Leu Glu Leu Ala Ala Lys Ser Pro Asp Pro Ala Val Leu Pro His Thr
            260                 265                 270

Glu Glu Leu Arg Lys His Tyr Thr Leu Asp Arg Ser Ala
        275                 280                 285

<210> SEQ ID NO 3
<211> LENGTH: 900
<212> TYPE: DNA
<213> ORGANISM: Artificial Sequence
<220> FEATURE:
<223> OTHER INFORMATION: synthetic DNA

<400> SEQUENCE: 3

| | | | | | |
|---|---|---|---|---|---|
| atgaaaagct | attccttggg | caagtttgag | gaccgttcta | ttgacagcct | gatcgaagaa | 60 |
| gcgtccggtc | tgccggacag | cgcgtattct | tctgcgtacc | aagagtacag | catcggtctg | 120 |
| tgggacaccg | ccacgctgtg | gaacgaacgt | ggcaacgaga | gcggcgaggt | tagcgagcac | 180 |
| gcggcagccg | ctgcgccgac | cgcaattggt | cgtagcaccc | cgcgtctgaa | cgaatttgta | 240 |
| cgtgccaagt | tcaatgtcga | tgtcctgcgt | gcggttcgct | tgttcagagc | gcgtcagggt | 300 |
| gcaattatca | tcccgcaccg | cgattacctg | gagcatagca | atggttttg | ccgtattcac | 360 |
| cttccgctgg | ttacgacccc | gggtgcgcgt | aatagcgaga | taacgaagt | gtatcgcatg | 420 |
| ctgcctggcg | agctgtggtt | cctggattca | aacgaagtgc | acagcggtgg | cgttctggac | 480 |
| agcggtacgc | gcattcacct | cgttttagat | ttcacccacg | agcataatga | aatccggct | 540 |
| gcagtgctga | gaacgccga | ccgttttgcgt | ccgatcgcgc | gtgacccgcg | catctcgcgc | 600 |
| tccaaactgg | atcacgaagc | gctggagagc | ctgatccgcg | gtggccgtgt | cgtcactctg | 660 |
| gcgatgtggc | cagctctggt | gcagatgctg | gcacgcattc | atctgaccag | cgacgcacat | 720 |
| ccggccgagc | tgtacgactg | gttggatgac | ctggcggacc | gcagcggcaa | cgatgagctg | 780 |
| gttgcagaag | cgcgtcgtat | gcgtcgttac | tttctgaccg | atggtattag | ccgtacgccg | 840 |
| agcttcgaac | gctttggcg | cgaactggat | gccgctcgta | aggtgagtt | ggtgagctaa | 900 |

<210> SEQ ID NO 4
<211> LENGTH: 299
<212> TYPE: PRT
<213> ORGANISM: Segniliparus rugosus

<400> SEQUENCE: 4

Met Lys Ser Tyr Ser Leu Gly Lys Phe Glu Asp Arg Ser Ile Asp Ser
1               5                   10                  15

Leu Ile Glu Glu Ala Ser Gly Leu Pro Asp Ser Ala Tyr Ser Ser Ala
            20                  25                  30

Tyr Gln Glu Tyr Ser Ile Gly Leu Trp Asp Thr Ala Thr Leu Trp Asn
        35                  40                  45

Glu Arg Gly Asn Glu Ser Gly Glu Val Ser Glu His Ala Ala Ala Ala
    50                  55                  60

-continued

```
Ala Pro Thr Ala Ile Gly Arg Ser Thr Pro Arg Leu Asn Glu Phe Val
 65                  70                  75                  80

Arg Ala Lys Phe Asn Val Asp Val Leu Arg Ala Val Arg Leu Phe Arg
                 85                  90                  95

Ala Arg Gln Gly Ala Ile Ile Ile Pro His Arg Asp Tyr Leu Glu His
            100                 105                 110

Ser Asn Gly Phe Cys Arg Ile His Leu Pro Leu Val Thr Thr Pro Gly
        115                 120                 125

Ala Arg Asn Ser Glu Asn Glu Val Tyr Arg Met Leu Pro Gly Glu
    130                 135                 140

Leu Trp Phe Leu Asp Ser Asn Glu Val His Ser Gly Gly Val Leu Asp
145                 150                 155                 160

Ser Gly Thr Arg Ile His Leu Val Leu Asp Phe Thr His Glu His Asn
                165                 170                 175

Glu Asn Pro Ala Ala Val Leu Lys Asn Ala Asp Arg Leu Arg Pro Ile
            180                 185                 190

Ala Arg Asp Pro Arg Ile Ser Arg Ser Lys Leu Asp His Glu Ala Leu
        195                 200                 205

Glu Ser Leu Ile Arg Gly Gly Arg Val Val Thr Leu Ala Met Trp Pro
    210                 215                 220

Ala Leu Val Gln Met Leu Ala Arg Ile His Leu Thr Ser Asp Ala His
225                 230                 235                 240

Pro Ala Glu Leu Tyr Asp Trp Leu Asp Leu Ala Asp Arg Ser Gly
                245                 250                 255

Asn Asp Glu Leu Val Ala Glu Ala Arg Arg Met Arg Arg Tyr Phe Leu
            260                 265                 270

Thr Asp Gly Ile Ser Arg Thr Pro Ser Phe Glu Arg Phe Trp Arg Glu
        275                 280                 285

Leu Asp Ala Ala Arg Lys Gly Glu Leu Val Ser
    290                 295

<210> SEQ ID NO 5
<211> LENGTH: 873
<212> TYPE: DNA
<213> ORGANISM: Artificial Sequence
<220> FEATURE:
<223> OTHER INFORMATION: synthetic DNA

<400> SEQUENCE: 5
atgcgtactc aatacgttgc ggcattggaa ttggatgagg gtcgtctggc gaaagacttg      60
gaaaccagcg cttctttcaa ctattccgag gcttacagca actacctgat ggtggcccg     120 tggaaatcgg caatgttgta cagcgccggt ggtgacgctg gcgatggcct gctgacggac    180
tatgactacc gccagagcag cgacttcacg gattatggcc gtcagatgcc gtatctgcaa    240
gagttaatct caacgagcgt tgacctgagc cgtctgacct tgtgcgtct ggcgcgtttt     300 gcgaaatctg tgatcgtccc gcaccgcgac ttcctggagc tggaagaaat tccagaggat    360
aagcgcagcg cgcatcgcct gcacattccg ctggccaccc acgaagagtg cttcttcagc    420
gaagataatg ttgtttaccg catgcgtgcc ggtgagctgt ggtacttcga cgcgagccgt    480
atccattccg tcgtgtcctt tgcagaggaa ccgcgcatcc acctgatttt cgattttgcg    540
gatagaccgg gtgccggtag cctggtcacg gttccgggcg agccggaagg tgcaggcgtg    600
ccagcagcga gcgcggttga ccgtccgcag ctgagcgatg ctgagcgtgc ggccctggcg    660
cgtctggccg acgtcctgac catggatacc tttagcgaaa tcttctctgt cctggttaag    720
```

| aagcattttc gccgtgacgg tggcgagcac tttgtgtggg ataccctgac cgcgctggcg | 780 |
| cgtgcatgtc cggacccggc agtgctgcct cacacccagg aactgcgtcg ttatttcacg | 840 |
| ctggagcgcc cgagcggtag cggtcaagcg taa | 873 |

<210> SEQ ID NO 6
<211> LENGTH: 290
<212> TYPE: PRT
<213> ORGANISM: Catenulispora acidiphila

<400> SEQUENCE: 6

```
Met Arg Thr Gln Tyr Val Ala Ala Leu Glu Leu Asp Glu Gly Arg Leu
1               5                   10                  15

Ala Lys Asp Leu Glu Thr Ser Ala Ser Phe Asn Tyr Ser Glu Ala Tyr
            20                  25                  30

Ser Asn Tyr Leu Ile Gly Gly Pro Trp Lys Ser Ala Met Leu Tyr Ser
        35                  40                  45

Ala Gly Gly Asp Ala Gly Asp Gly Leu Leu Thr Asp Tyr Asp Tyr Arg
    50                  55                  60

Gln Ser Ser Asp Phe Thr Asp Tyr Gly Arg Gln Met Pro Tyr Leu Gln
65                  70                  75                  80

Glu Leu Ile Ser Thr Ser Val Asp Leu Ser Arg Leu Thr Phe Val Arg
                85                  90                  95

Leu Ala Arg Phe Ala Lys Ser Val Ile Val Pro His Arg Asp Phe Leu
            100                 105                 110

Glu Leu Glu Glu Ile Pro Glu Asp Lys Arg Ser Ala His Arg Leu His
        115                 120                 125

Ile Pro Leu Ala Thr His Glu Glu Cys Phe Phe Ser Glu Asp Asn Val
    130                 135                 140

Val Tyr Arg Met Arg Ala Gly Glu Leu Trp Tyr Phe Asp Ala Ser Arg
145                 150                 155                 160

Ile His Ser Val Val Ser Phe Ala Glu Glu Pro Arg Ile His Leu Ile
                165                 170                 175

Phe Asp Phe Ala Asp Arg Pro Gly Ala Gly Ser Leu Val Thr Val Pro
            180                 185                 190

Gly Glu Pro Glu Gly Ala Gly Val Pro Ala Ala Ser Ala Val Asp Arg
        195                 200                 205

Pro Gln Leu Ser Asp Ala Glu Arg Ala Ala Leu Ala Arg Leu Ala Asp
    210                 215                 220

Val Leu Thr Met Asp Thr Phe Ser Glu Ile Phe Ser Val Leu Val Lys
225                 230                 235                 240

Lys His Phe Arg Arg Asp Gly Gly Glu His Phe Val Trp Asp Thr Leu
                245                 250                 255

Thr Ala Leu Ala Arg Ala Cys Pro Asp Pro Ala Val Leu Pro His Thr
            260                 265                 270

Gln Glu Leu Arg Arg Tyr Phe Thr Leu Glu Arg Pro Ser Gly Ser Gly
        275                 280                 285

Gln Ala
    290
```

<210> SEQ ID NO 7
<211> LENGTH: 885
<212> TYPE: DNA
<213> ORGANISM: Artificial Sequence
<220> FEATURE:
<223> OTHER INFORMATION: synthetic DNA

<400> SEQUENCE: 7

```
atgatgagcg caaaactgct ggcaagcatt gaattgaacc aagaacagat cgagcatgat      60
ctgaatattg ttggtagcga gatcctggac gtggcgtaca gcgagtatgc gtgcggcaat     120
tggggtacca ttaccctgtg gaaccacagc ggcgatgctg gcgaccagac gagccgcgaa     180
tacgttggtc aggcccgtcc gactgagctg ggccagcaat tagactgcat taatcagctg     240
atccgtaaca atttcaacat cagcctgatc aagagcgtgc gcatcttccg tagctataac     300
ggtggtgcga tctatccgca cattgactac ttggaattca accaaggttt taagcgcgtg     360
cacctggttc tgaaatccga ccgttcatgt ctgaatagcg aagagaacac ggtttatcac     420
atgctgcctg gtgaagtgtg gtttgtcgat ggtcatagcg cgcactcggc gatgagcctg     480
agccgtgtcg gcaagtactc gctggtcctg gactttgatt ctggcgccaa attcgaagat     540
ctgtattctg agagccacac cctgtgtgtt gataacctgg agccgacat tatccatgac      600
cgccagccac tgccgaccag cctgcgtgat agcctggcac acattgctga gcatgcggat     660
gaattcaata tccaatccat tctgttcctg gccacccgtt tcactttag ctacgcagtg      720
agcattcgtg agtacttcca actcctggac gagtgctttt ctcgcaaccc gtacaagtcc     780
gttcgcgagc gttacgaagc gctgaaagac attttggtgc gtagcggtta taccagccac     840
aatgtcaatc atttcaacag cttgtccggt gtcacgatcg gctaa                    885
```

<210> SEQ ID NO 8
<211> LENGTH: 294
<212> TYPE: PRT
<213> ORGANISM: Xenorhabdus doucetiae

<400> SEQUENCE: 8

```
Met Met Ser Ala Lys Leu Leu Ala Ser Ile Glu Leu Asn Gln Glu Gln
1               5                   10                  15

Ile Glu His Asp Leu Asn Ile Val Gly Ser Glu Ile Leu Asp Val Ala
            20                  25                  30

Tyr Ser Glu Tyr Ala Cys Gly Asn Trp Gly Thr Ile Thr Leu Trp Asn
        35                  40                  45

His Ser Gly Asp Ala Gly Asp Gln Thr Ser Arg Glu Tyr Val Gly Gln
    50                  55                  60

Ala Arg Pro Thr Glu Leu Gly Gln Gln Leu Asp Cys Ile Asn Gln Leu
65                  70                  75                  80

Ile Arg Asn Asn Phe Asn Ile Ser Leu Ile Lys Ser Val Arg Ile Phe
                85                  90                  95

Arg Ser Tyr Asn Gly Gly Ala Ile Tyr Pro His Ile Asp Tyr Leu Glu
            100                 105                 110

Phe Asn Gln Gly Phe Lys Arg Val His Leu Val Leu Lys Ser Asp Arg
        115                 120                 125

Ser Cys Leu Asn Ser Glu Glu Asn Thr Val Tyr His Met Leu Pro Gly
    130                 135                 140

Glu Val Trp Phe Val Asp Gly His Ser Ala His Ser Ala Met Ser Leu
145                 150                 155                 160

Ser Arg Val Gly Lys Tyr Ser Leu Val Leu Asp Phe Asp Ser Gly Ala
                165                 170                 175

Lys Phe Glu Asp Leu Tyr Ser Glu Ser His Thr Leu Cys Val Asp Asn
            180                 185                 190

Leu Glu Pro Asp Ile Ile His Asp Arg Gln Pro Leu Pro Thr Ser Leu
        195                 200                 205
```

Arg Asp Ser Leu Ala His Ile Ala Glu His Ala Asp Glu Phe Asn Ile
    210                 215                 220

Gln Ser Ile Leu Phe Leu Ala Thr Arg Phe His Phe Ser Tyr Ala Val
225                 230                 235                 240

Ser Ile Arg Glu Tyr Phe Gln Leu Leu Asp Glu Cys Phe Ser Arg Asn
                245                 250                 255

Pro Tyr Lys Ser Val Arg Glu Arg Tyr Glu Ala Leu Lys Asp Ile Leu
            260                 265                 270

Val Arg Ser Gly Tyr Thr Ser His Asn Val Asn His Phe Asn Ser Leu
        275                 280                 285

Ser Gly Val Thr Ile Gly
    290

<210> SEQ ID NO 9
<211> LENGTH: 843
<212> TYPE: DNA
<213> ORGANISM: Artificial Sequence
<220> FEATURE:
<223> OTHER INFORMATION: synthetic DNA

<400> SEQUENCE: 9
atgagcaccc attttctcgg caaggtaaag tttgatgaag cgcgtttggc agaggacttg      60
agcaccctgg aagtggctga gtttagcagc gcctacagcg actttgcatg cggcaaatgg     120
gaagcgtgcg tcctgcgcaa ccgcaccggt atgcaagaag aagatatcgt tgttagccac     180
aatgctccgg cgctggcgac gccgctgagc aagtccctgc cgtatctgaa cgagctggtg     240
gaaacccatt tcgactgtag cgccgtgcgt tacacgcgca ttgttcgtgt ctctgagaac     300
gcatgtatca ttccgcattc tgactatctg gagttggatg aaacgttcac gcgcctgcac     360
ctggttctgg acacgaatag cggttgtgcg ataccgaag aggataagat tttccacatg      420
ggtctgggcg agatctggtt cctggatgct atgctgccgc acagcgccgc atgctttagc     480
aaaactccgc gtctgcactt gatgattgat ttcgaggcga ccgcgttccc agagagcttt     540
ttgcgtaacg ttgagcagcc ggtcaccacc cgtgatatgg tggacccgcg taaagagctg     600
accgacgagg tgatcgaagg tatcctgggc ttttccatca tcattagcga ggcaaattac     660
cgtgagattg tctccattct ggcgaaactg cacttctttt acaaggcgga ttgccgcagc     720
atgtacgact ggctgaaaga aatctgcaaa cgtcgtggtg accctgccct gattgaaaag     780
accgcgtcgc tggagcgctt cttcctgggt catcgtgaac gcggtgaggt tatgacgtat     840
taa                                                                   843

<210> SEQ ID NO 10
<211> LENGTH: 280
<212> TYPE: PRT
<213> ORGANISM: Sinorhizobium meliloti

<400> SEQUENCE: 10

Met Ser Thr His Phe Leu Gly Lys Val Lys Phe Asp Glu Ala Arg Leu
1               5                   10                  15

Ala Glu Asp Leu Ser Thr Leu Glu Val Ala Glu Phe Ser Ala Tyr
            20                  25                  30

Ser Asp Phe Ala Cys Gly Lys Trp Glu Ala Cys Val Leu Arg Asn Arg
        35                  40                  45

Thr Gly Met Gln Glu Glu Asp Ile Val Val Ser His Asn Ala Pro Ala
    50                  55                  60

Leu Ala Thr Pro Leu Ser Lys Ser Leu Pro Tyr Leu Asn Glu Leu Val
65                  70                  75                  80

Glu Thr His Phe Asp Cys Ser Ala Val Arg Tyr Thr Arg Ile Val Arg
                85                  90                  95

Val Ser Glu Asn Ala Cys Ile Ile Pro His Ser Asp Tyr Leu Glu Leu
            100                 105                 110

Asp Glu Thr Phe Thr Arg Leu His Leu Val Leu Asp Thr Asn Ser Gly
        115                 120                 125

Cys Ala Asn Thr Glu Glu Asp Lys Ile Phe His Met Gly Leu Gly Glu
130                 135                 140

Ile Trp Phe Leu Asp Ala Met Leu Pro His Ser Ala Ala Cys Phe Ser
145                 150                 155                 160

Lys Thr Pro Arg Leu His Leu Met Ile Asp Phe Glu Ala Thr Ala Phe
                165                 170                 175

Pro Glu Ser Phe Leu Arg Asn Val Glu Gln Pro Val Thr Thr Arg Asp
            180                 185                 190

Met Val Asp Pro Arg Lys Glu Leu Thr Asp Glu Val Ile Glu Gly Ile
        195                 200                 205

Leu Gly Phe Ser Ile Ile Ile Ser Glu Ala Asn Tyr Arg Glu Ile Val
210                 215                 220

Ser Ile Leu Ala Lys Leu His Phe Phe Tyr Lys Ala Asp Cys Arg Ser
225                 230                 235                 240

Met Tyr Asp Trp Leu Lys Glu Ile Cys Lys Arg Arg Gly Asp Pro Ala
                245                 250                 255

Leu Ile Glu Lys Thr Ala Ser Leu Glu Arg Phe Phe Leu Gly His Arg
            260                 265                 270

Glu Arg Gly Glu Val Met Thr Tyr
        275                 280

<210> SEQ ID NO 11
<211> LENGTH: 993
<212> TYPE: DNA
<213> ORGANISM: Artificial Sequence
<220> FEATURE:
<223> OTHER INFORMATION: synthetic DNA

<400> SEQUENCE: 11
atgagcgata aaggtgcaac gttggacatg agcctgtttt tcggtacgcc agaggaaaaa      60
ggctatttct gtaccgaact gttgcgtctg ctgaagttgc gtggtggtgt taagattcag     120
aatcactcta tcccggacga agatatccac aagctgttcg acatgagccg taagtttttc     180
gccttaccgc tggagactaa aatggaagcg aaacatccgc cgcaagctaa tccgaaccgc     240
ggctacagct ttatcggcca ggagaatgtc gccaacatca gcggttacga aaaggcctg     300 ggccctggta gacccgtga tatcaaagaa accctggaca tgggttccgc acaggatgat     360
ttggtcgaca acctgtggat tccggaggaa agcctgccgg ttttcgtgg ctttatggaa      420 tccttctacg aaaaagcatt caagaccgaa atgcaactcc tgagcgcgtt ggcaattgcg     480
ctgggtgttt cggaggacca catgaaaacg ctgcacaatc gcgcggagaa cgagttccgt     540
ctgctgcatt atccggctat cccggcgacc gagctggcag atggtaccgc gacgcgcatt     600
gccgaacaca ccgatttttgg tacgattacc atgctgtttc aagacagcgt cggcggtctg     660
caagtggagg accaaaccca gccgggtgtg ttccgtagcg tggagagcga aaagccgacc     720
gatatcattc tgaatatcgg cgacagcctg cagcgcctga ccaatgacac gttcagagcg     780

```
gcgtgccacc gtgtcacgta cccgccagct attaaggcgc gtgataacgt gcagatcccg    840
gagcgctata gcattgcata ctttgttaaa cctaaccgtc atgcctctct gcttccgctg    900
aaagagttca tcaccgacgc gaccccgtgc cgttatgaag atgttacggc gtgggagtgg    960
aacaatcgcc gtattactaa gctgtttggc taa                                 993
```

<210> SEQ ID NO 12
<211> LENGTH: 330
<212> TYPE: PRT
<213> ORGANISM: Colletotrichum gloeosporioides

<400> SEQUENCE: 12

```
Met Ser Asp Lys Gly Ala Thr Leu Asp Met Ser Leu Phe Phe Gly Thr
1               5                   10                  15

Pro Glu Glu Lys Gly Tyr Phe Cys Thr Glu Leu Leu Arg Leu Leu Lys
            20                  25                  30

Leu Arg Gly Gly Val Lys Ile Gln Asn His Ser Ile Pro Asp Glu Asp
        35                  40                  45

Ile His Lys Leu Phe Asp Met Ser Arg Lys Phe Phe Ala Leu Pro Leu
    50                  55                  60

Glu Thr Lys Met Glu Ala Lys His Pro Pro Gln Ala Asn Pro Asn Arg
65                  70                  75                  80

Gly Tyr Ser Phe Ile Gly Gln Glu Asn Val Ala Asn Ile Ser Gly Tyr
                85                  90                  95

Glu Lys Gly Leu Gly Pro Gly Lys Thr Arg Asp Ile Lys Glu Thr Leu
            100                 105                 110

Asp Met Gly Ser Ala Gln Asp Asp Leu Val Asp Asn Leu Trp Ile Pro
        115                 120                 125

Glu Glu Ser Leu Pro Gly Phe Arg Gly Phe Met Glu Ser Phe Tyr Glu
    130                 135                 140

Lys Ala Phe Lys Thr Glu Met Gln Leu Leu Ser Ala Leu Ala Ile Ala
145                 150                 155                 160

Leu Gly Val Ser Glu Asp His Met Lys Thr Leu His Asn Arg Ala Glu
                165                 170                 175

Asn Glu Phe Arg Leu Leu His Tyr Pro Ala Ile Pro Ala Thr Glu Leu
            180                 185                 190

Ala Asp Gly Thr Ala Thr Arg Ile Ala Glu His Thr Asp Phe Gly Thr
        195                 200                 205

Ile Thr Met Leu Phe Gln Asp Ser Val Gly Gly Leu Gln Val Glu Asp
    210                 215                 220

Gln Thr Gln Pro Gly Val Phe Arg Ser Val Glu Ser Glu Lys Pro Thr
225                 230                 235                 240

Asp Ile Ile Leu Asn Ile Gly Asp Ser Leu Gln Arg Leu Thr Asn Asp
                245                 250                 255

Thr Phe Arg Ala Ala Cys His Arg Val Thr Tyr Pro Pro Ala Ile Lys
            260                 265                 270

Ala Arg Asp Asn Val Gln Ile Pro Glu Arg Tyr Ser Ile Ala Tyr Phe
        275                 280                 285

Val Lys Pro Asn Arg His Ala Ser Leu Leu Pro Leu Lys Glu Phe Ile
    290                 295                 300

Thr Asp Ala Thr Pro Cys Arg Tyr Glu Asp Val Thr Ala Trp Glu Trp
305                 310                 315                 320

Asn Asn Arg Arg Ile Thr Lys Leu Phe Gly
                325                 330
```

<210> SEQ ID NO 13
<211> LENGTH: 987
<212> TYPE: DNA
<213> ORGANISM: Artificial Sequence
<220> FEATURE:
<223> OTHER INFORMATION: synthetic DNA

<400> SEQUENCE: 13

```
atgagccaag cccttgattt gtctctgctg aaaggtagcc cggaagaacg tgatgaagtt    60
tccgcagccc tgctggacac cttgaaaacc cgtggtgttg cgaaactgaa gaaccacggt   120
ctgccggagg atctgattgc cgagatgttc gattacacgc gccgtttctt cagcttgtcc   180
ctggaggaca agatgacggc gaagcacccg ccagaggcga acccgaaccg cggctatagc   240
tacgttggcc aggagagcgt gtctagcatc tcaggttatg aaaagggttt accgcaaggt   300
aagactatcc gtgacattaa agaaaccctg gacatgggca gccgcacga ctcgctggtc   360
gataacattt gggtggcaga gagaagctg ccgggttttc gcaagttcat ggaagatttc   420
tacgagagct gtttcaaagt ggaactggag attctggatg ccctggcgca ggcgctggaa   480
atcagcgctc ctgatctgcg tctgttgcac aataaagcgg agaatgagtt ccgcctgctg   540
cattaccctg ctgttccggc tagcgcactg gaggatggca ccgcaacgcg tatcgcggag   600
cacacggact ttggcaccat taccatgttg tttcaggaca gcaccggcgg tctgcaagtg   660
gaggaccaaa ccaatctggg tacctttcat gacgtcgtta gcggtggcaa aagcgaaatc   720
attctgaaca tcggcgatag cctgcagcgt ctgaccaatg acacgttcat ggcggcgtgc   780
catcgtgtta cgtatccgcc gaccgtcaaa gtgggttctg acgtcgtgat ccggagcgc    840
tactccgtcg cctattttgc gaagccgaat cgtatcgcga gcctgtttcc gctgaaaaag   900
tttatcaccc cagcaacgcc gtgcaagtat gaagatatta ctgcatggga ctacaacaat   960
ctccgtatcg cgaaactgtt cagctaa                                      987
```

<210> SEQ ID NO 14
<211> LENGTH: 328
<212> TYPE: PRT
<213> ORGANISM: Penicillium chrysogenum

<400> SEQUENCE: 14

```
Met Ser Gln Ala Leu Asp Leu Ser Leu Leu Lys Gly Ser Pro Glu Glu
1               5                   10                  15

Arg Asp Glu Val Ser Ala Ala Leu Leu Asp Thr Leu Lys Thr Arg Gly
            20                  25                  30

Val Ala Lys Leu Lys Asn His Gly Leu Pro Glu Asp Leu Ile Ala Glu
        35                  40                  45

Met Phe Asp Tyr Thr Arg Arg Phe Phe Ser Leu Ser Leu Glu Asp Lys
    50                  55                  60

Met Thr Ala Lys His Pro Pro Glu Ala Asn Pro Asn Arg Gly Tyr Ser
65                  70                  75                  80

Tyr Val Gly Gln Glu Ser Val Ser Ser Ile Ser Gly Tyr Glu Lys Gly
                85                  90                  95

Leu Pro Gln Gly Lys Thr Ile Arg Asp Ile Lys Glu Thr Leu Asp Met
            100                 105                 110

Gly Ser Pro His Asp Ser Leu Val Asp Asn Ile Trp Val Ala Glu Glu
        115                 120                 125

Lys Leu Pro Gly Phe Arg Lys Phe Met Glu Asp Phe Tyr Glu Ser Cys
    130                 135                 140
```

```
Phe Lys Val Glu Leu Glu Ile Leu Asp Ala Leu Ala Gln Ala Leu Glu
145                 150                 155                 160

Ile Ser Ala Pro Asp Leu Arg Leu Leu His Asn Lys Ala Glu Asn Glu
                165                 170                 175

Phe Arg Leu Leu His Tyr Pro Ala Val Pro Ala Ser Ala Leu Glu Asp
            180                 185                 190

Gly Thr Ala Thr Arg Ile Ala Glu His Thr Asp Phe Gly Thr Ile Thr
        195                 200                 205

Met Leu Phe Gln Asp Ser Thr Gly Gly Leu Gln Val Glu Asp Gln Thr
    210                 215                 220

Asn Leu Gly Thr Phe His Asp Val Val Ser Gly Gly Lys Ser Glu Ile
225                 230                 235                 240

Ile Leu Asn Ile Gly Asp Ser Leu Gln Arg Leu Thr Asn Asp Thr Phe
                245                 250                 255

Met Ala Ala Cys His Arg Val Thr Tyr Pro Pro Thr Val Lys Val Gly
            260                 265                 270

Ser Asp Val Val Ile Pro Glu Arg Tyr Ser Val Ala Tyr Phe Ala Lys
        275                 280                 285

Pro Asn Arg Ile Ala Ser Leu Phe Pro Leu Lys Lys Phe Ile Thr Pro
    290                 295                 300

Ala Thr Pro Cys Lys Tyr Glu Asp Ile Thr Ala Trp Asp Tyr Asn Asn
305                 310                 315                 320

Leu Arg Ile Ala Lys Leu Phe Ser
                325

<210> SEQ ID NO 15
<211> LENGTH: 1014
<212> TYPE: DNA
<213> ORGANISM: Artificial Sequence
<220> FEATURE:
<223> OTHER INFORMATION: synthetic DNA

<400> SEQUENCE: 15
atggctgccc tgaacgttga caccctggac atgtcccttt tcttcggtac ccctgatcag      60
aagaaagatt tctgcgactc gctgctgcgc ctgctgaaaa agcgtggcgg tgtgaagctc     120
gttaaccact ctattccgag cgaggatatc catgagctgt ttgcccaaac caaacgcttc     180
tttgaactgc cgctggaaac gaaaatgatt gcgaaacatc cgccacaggc gaatccgaac     240
cgtggttaca gcttcgtggg ccaggaaaac gtggcgaata tctccggtta cgagaagggt     300
ctgggcccac aaaccacgcg tgacattaaa gagactgttg atttcggtag cgcgacggac     360
gagctggtcg acaatatctg ggttccggag gacaaactgc cgggttttcg caagttcatg     420
gaaggtttct acgaaaaggc gtttaagacc gaaatgcagc tgttggaagc tttggctatc     480
gcactgggcg tttcagcaga ccacctgaaa agcatccaca atcgtgctga aaacgagttt     540
cgtatcttgc actatccggc agtgccggcg tccgagctgg cggatggcac tgcaacgcgc     600
atcgcagagc acaccgattt cggtaccatt acgatgctgt tccaggacag cgtcggtggc     660
ttacaggtcg aagatcaaga gaatttgggc catttcaaca acgtggagag cgcggcaccg     720
acggacatta tcctgaatat tggcgacagc ctgcaacgtc tgaccaatga tacctttaaa     780
gccgcgtgtc atcgtgtcac ctaccctccg agcattaagg cgagcgacgg tgaacaagtt     840
attccggagc gctatagcat cgcctatttt gcaaagccga accgttctgc cagcctgttc     900
ccgctgaaag agtttattga ggaaggtatg ccgtgcaagt acgaagatgt caccgcgtgg     960
gagtggaata accgtcgtat cgagaagctg tttagcagcg atgcgaaagc gtaa         1014
```

```
<210> SEQ ID NO 16
<211> LENGTH: 337
<212> TYPE: PRT
<213> ORGANISM: Gibberella zeae

<400> SEQUENCE: 16
```

| | | | | | | | | | | | | | | |
|---|---|---|---|---|---|---|---|---|---|---|---|---|---|---|
|Met|Ala|Ala|Leu|Asn|Val|Asp|Thr|Leu|Asp|Met|Ser|Leu|Phe|Phe|Gly|
|1| | | |5| | | | |10| | | | |15|

Thr Pro Asp Gln Lys Lys Asp Phe Cys Asp Ser Leu Leu Arg Leu Leu
            20                  25                  30

Lys Lys Arg Gly Gly Val Lys Leu Val Asn His Ser Ile Pro Ser Glu
        35                  40                  45

Asp Ile His Glu Leu Phe Ala Gln Thr Lys Arg Phe Phe Glu Leu Pro
    50                  55                  60

Leu Glu Thr Lys Met Ile Ala Lys His Pro Pro Gln Ala Asn Pro Asn
65                  70                  75                  80

Arg Gly Tyr Ser Phe Val Gly Gln Glu Asn Val Ala Asn Ile Ser Gly
                85                  90                  95

Tyr Glu Lys Gly Leu Gly Pro Gln Thr Thr Arg Asp Ile Lys Glu Thr
            100                 105                 110

Val Asp Phe Gly Ser Ala Thr Asp Glu Leu Val Asp Asn Ile Trp Val
        115                 120                 125

Pro Glu Asp Lys Leu Pro Gly Phe Arg Lys Phe Met Glu Gly Phe Tyr
    130                 135                 140

Glu Lys Ala Phe Lys Thr Glu Met Gln Leu Leu Glu Ala Leu Ala Ile
145                 150                 155                 160

Ala Leu Gly Val Ser Ala Asp His Leu Lys Ser Ile His Asn Arg Ala
                165                 170                 175

Glu Asn Glu Phe Arg Ile Leu His Tyr Pro Ala Val Pro Ala Ser Glu
            180                 185                 190

Leu Ala Asp Gly Thr Ala Thr Arg Ile Ala Glu His Thr Asp Phe Gly
        195                 200                 205

Thr Ile Thr Met Leu Phe Gln Asp Ser Val Gly Gly Leu Gln Val Glu
    210                 215                 220

Asp Gln Glu Asn Leu Gly His Phe Asn Asn Val Glu Ser Ala Ala Pro
225                 230                 235                 240

Thr Asp Ile Ile Leu Asn Ile Gly Asp Ser Leu Gln Arg Leu Thr Asn
                245                 250                 255

Asp Thr Phe Lys Ala Ala Cys His Arg Val Thr Tyr Pro Pro Ser Ile
            260                 265                 270

Lys Ala Ser Asp Gly Glu Gln Val Ile Pro Glu Arg Tyr Ser Ile Ala
        275                 280                 285

Tyr Phe Ala Lys Pro Asn Arg Ser Ala Ser Leu Phe Pro Leu Lys Glu
    290                 295                 300

Phe Ile Glu Glu Gly Met Pro Cys Lys Tyr Glu Asp Val Thr Ala Trp
305                 310                 315                 320

Glu Trp Asn Asn Arg Arg Ile Glu Lys Leu Phe Ser Ser Asp Ala Lys
                325                 330                 335

Ala

```
<210> SEQ ID NO 17
<211> LENGTH: 831
<212> TYPE: DNA
<213> ORGANISM: Artificial Sequence
```

<220> FEATURE:
<223> OTHER INFORMATION: synthetic DNA

<400> SEQUENCE: 17

```
atggaaagca aaatcattgg caaggtcaat ttcgaggaac atctgctgga caaagaactg      60
aagctgatcg atacgtttga gttcaacgac tcgtacagcg agtatgcgtc cggtatttgg     120
aaaacctgta tgttgtggaa ccgtagcggc cagaaagacg accacctgag cattgagcat     180
gacacctatg ttaaaccgac tgagtatggt aagcaactgg cgtacgtgaa cgaaattatc     240
gcgaatacgt tcaaaaaaga acacattaag accgtgcgtc tgtttatgtg cattaacggc     300
ctgattatcc cgcataaaga ttacctggaa ttcaaaaaag ctttacccg cattcacatt      360
ccactgaaga tcaacgaaca cgcgctcacg tccgaggaag atgtcgttta acatgcag       420
aaaggtgaga tctggtttat cgagggtcgt aagattcaca gcgctgccaa cttcagcaag     480
gttaagcgta tcaatttggt cattgatttc gcaccggaca tcccgtttga agaattattc     540
ctgaattctg agaattacca gccgaacctg attcctaaga ttagccagcg cacccagctg     600
aaagaggaag aattgggcta tatcaagggt ctgagcaaga tcatcaacga aatgaacttt     660
gatgacatcc tgagcatcct gtctaagatt cactttacc gcaatgtgag cagcgaactg      720
gtgttcggtt ggctggatga aatcgcaacg gcgagcaaca attacaatat ccaacgtaaa     780
gcccaagagg ttaccgatct gttgattcgt aagggtccga ttaacaatta a              831
```

<210> SEQ ID NO 18
<211> LENGTH: 276
<212> TYPE: PRT
<213> ORGANISM: Kordia jejudonensis

<400> SEQUENCE: 18

```
Met Glu Ser Lys Ile Ile Gly Lys Val Asn Phe Glu Glu His Leu Leu
1               5                   10                  15
Asp Lys Glu Leu Lys Leu Ile Asp Thr Phe Glu Phe Asn Asp Ser Tyr
            20                  25                  30
Ser Glu Tyr Ala Ser Gly Ile Trp Lys Thr Cys Met Leu Trp Asn Arg
        35                  40                  45
Ser Gly Gln Lys Asp Asp His Leu Ser Ile Glu His Asp Thr Tyr Val
    50                  55                  60
Lys Pro Thr Glu Tyr Gly Lys Gln Leu Ala Tyr Val Asn Glu Ile Ile
65                  70                  75                  80
Ala Asn Thr Phe Lys Lys Glu His Ile Lys Thr Val Arg Leu Phe Met
                85                  90                  95
Cys Ile Asn Gly Leu Ile Ile Pro His Lys Asp Tyr Leu Glu Phe Lys
            100                 105                 110
Lys Gly Phe Thr Arg Ile His Ile Pro Leu Lys Ile Asn Glu His Ala
        115                 120                 125
Leu Thr Ser Glu Glu Asp Val Val Tyr Asn Met Gln Lys Gly Glu Ile
    130                 135                 140
Trp Phe Ile Glu Gly Arg Lys Ile His Ser Ala Ala Asn Phe Ser Lys
145                 150                 155                 160
Val Lys Arg Ile Asn Leu Val Ile Asp Phe Ala Pro Asp Ile Pro Phe
                165                 170                 175
Glu Glu Leu Phe Leu Asn Ser Glu Asn Tyr Gln Pro Asn Leu Ile Pro
            180                 185                 190
Lys Ile Ser Gln Arg Thr Gln Leu Lys Glu Glu Glu Leu Gly Tyr Ile
        195                 200                 205
```

```
Lys Gly Leu Ser Lys Ile Ile Asn Glu Met Asn Phe Asp Asp Ile Leu
        210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275

<210> SEQ ID NO 19
<211> LENGTH: 858
<212> TYPE: DNA
<213> ORGANISM: Artificial Sequence
<220> FEATURE:
<223> OTHER INFORMATION: synthetic DNA

<400> SEQUENCE: 19
atgagaacgc attatgtggg tgaagttgca ttggacctgg cacgtctgga ggctgatctg      60
gcaaccgctc gtagcctgga gtggagcgaa gcgtattcgg attacgtctt tggtggtagc     120
tggaaaagct gcatgctgtg ggcgcctggt ggcgatgccg gcgatggtgt tgtgacggac     180
tacgcgtacg accgtagcgc gggttttacg ccgcacgcag agcgcctgcc gtatctggca     240
gagcttattc gtgagactgc agatctggat cgcctgaatt tcgcgcgctt ggcgctggta     300
accaactctg tgattatccc gcaccgtgac ctgttggaat taagcgactt gccggacgaa     360
gctcgcaatg aacaccgtat gcacattccg ctggcgacca atgataactg cttcttcaac     420
gaggacaacg ttgtgtatcg tatgcgtcgt ggtgaagttt ggtttctgga tgccagccgt     480
attcatagcg tcgctgtcct gacggcgcag ccacgtatcc atctgatgct ggatttcgtg     540
gacacccccgg gtgcgggcag cttcacgcgc gttgcgggtg cggcgttga ggccggcatc     600
ccggtcgatc gcatcgtgac ccgtccgccg ctgggcgacg acgagcgtgc ggacctgttc     660
ggtgtcgccc cactcctgtc catggatacc ttcgacgaag tgttttccat tgttatcaag     720
aaacacttcc gtcgtgatgg tggcagcgac tttgtgtggg acaccatgct ggaactggcg     780
gcgaagtctc cggatccggc cgtcctgccg cataccgaag aactgcgcaa gcactacacc     840
ctggagcgca gcgcataa                                                   858

<210> SEQ ID NO 20
<211> LENGTH: 285
<212> TYPE: PRT
<213> ORGANISM: Micromonospora chokoriensis

<400> SEQUENCE: 20

Met Arg Thr His Tyr Val Gly Glu Val Ala Leu Asp Leu Ala Arg Leu
1               5                   10                  15

Glu Ala Asp Leu Ala Thr Ala Arg Ser Leu Glu Trp Ser Glu Ala Tyr
            20                  25                  30

Ser Asp Tyr Val Phe Gly Gly Ser Trp Lys Ser Cys Met Leu Trp Ala
        35                  40                  45

Pro Gly Gly Asp Ala Gly Asp Gly Val Val Thr Asp Tyr Ala Tyr Asp
    50                  55                  60

Arg Ser Ala Gly Phe Thr Pro His Ala Glu Arg Leu Pro Tyr Leu Ala
65                  70                  75                  80
```

-continued

```
Glu Leu Ile Arg Glu Thr Ala Asp Leu Asp Arg Leu Asn Phe Ala Arg
                85                  90                  95

Leu Ala Leu Val Thr Asn Ser Val Ile Ile Pro His Arg Asp Leu Leu
            100                 105                 110

Glu Leu Ser Asp Leu Pro Asp Glu Ala Arg Asn Glu His Arg Met His
        115                 120                 125

Ile Pro Leu Ala Thr Asn Asp Asn Cys Phe Phe Asn Glu Asp Asn Val
    130                 135                 140

Val Tyr Arg Met Arg Arg Gly Glu Val Trp Phe Leu Asp Ala Ser Arg
145                 150                 155                 160

Ile His Ser Val Ala Val Leu Thr Ala Gln Pro Arg Ile His Leu Met
                165                 170                 175

Leu Asp Phe Val Asp Thr Pro Gly Ala Gly Ser Phe Thr Arg Val Ala
            180                 185                 190

Gly Gly Gly Val Glu Ala Gly Ile Pro Val Asp Arg Ile Val Thr Arg
        195                 200                 205

Pro Pro Leu Gly Asp Asp Glu Arg Ala Asp Leu Phe Gly Val Ala Pro
    210                 215                 220

Leu Leu Ser Met Asp Thr Phe Asp Glu Val Phe Ser Ile Val Ile Lys
225                 230                 235                 240

Lys His Phe Arg Arg Asp Gly Gly Ser Asp Phe Val Trp Asp Thr Met
                245                 250                 255

Leu Glu Leu Ala Ala Lys Ser Pro Asp Pro Ala Val Leu Pro His Thr
            260                 265                 270

Glu Glu Leu Arg Lys His Tyr Thr Leu Glu Arg Ser Ala
        275                 280                 285
```

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
tttcatatga gcacccattt tctcggcaag gtaaag                          36

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
tttaagcttt taatacgtca taacctcacc gcg                             33

<210> SEQ ID NO 23
<211> LENGTH: 40
<212> TYPE: DNA
<213> ORGANISM: Artificial Sequence
<220> FEATURE:
<223> OTHER INFORMATION: primer

<400> SEQUENCE: 23
ggtaaaacat atgagaacgc agtttgtggg tgaagttgca                      40

<210> SEQ ID NO 24
<211> LENGTH: 40
<212> TYPE: DNA

```
<213> ORGANISM: Artificial Sequence
<220> FEATURE:
<223> OTHER INFORMATION: primer

<400> SEQUENCE: 24
tgcaacttca cccacaaact gcgttctcat atgttttacc                              40

<210> SEQ ID NO 25
<211> LENGTH: 41
<212> TYPE: DNA
<213> ORGANISM: Artificial Sequence
<220> FEATURE:
<223> OTHER INFORMATION: primer

<400> SEQUENCE: 25
aaaacatatg agaacgcatt atgtgggtga agttgcattg g                            41

<210> SEQ ID NO 26
<211> LENGTH: 41
<212> TYPE: DNA
<213> ORGANISM: Artificial Sequence
<220> FEATURE:
<223> OTHER INFORMATION: primer

<400> SEQUENCE: 26
ccaatgcaac ttcacccaca taatgcgttc tcatatgttt t                            41

<210> SEQ ID NO 27
<211> LENGTH: 41
<212> TYPE: DNA
<213> ORGANISM: Artificial Sequence
<220> FEATURE:
<223> OTHER INFORMATION: primer

<400> SEQUENCE: 27
ggaggctgat ctggcaaccg ctcgtagcct ggagtggagc g                            41

<210> SEQ ID NO 28
<211> LENGTH: 41
<212> TYPE: DNA
<213> ORGANISM: Artificial Sequence
<220> FEATURE:
<223> OTHER INFORMATION: primer

<400> SEQUENCE: 28
cgctccactc caggctacga gcggttgcca gatcagcctc c                            41

<210> SEQ ID NO 29
<211> LENGTH: 41
<212> TYPE: DNA
<213> ORGANISM: Artificial Sequence
<220> FEATURE:
<223> OTHER INFORMATION: primer

<400> SEQUENCE: 29
tggtggtagc tggaaaagcg cgatgctgtg ggcgcctggt g                            41

<210> SEQ ID NO 30
<211> LENGTH: 41
<212> TYPE: DNA
<213> ORGANISM: Artificial Sequence
<220> FEATURE:
<223> OTHER INFORMATION: primer

<400> SEQUENCE: 30
caccaggcgc ccacagcatc gcgcttttcc agctaccacc a                            41
```

<210> SEQ ID NO 31
<211> LENGTH: 41
<212> TYPE: DNA
<213> ORGANISM: Artificial Sequence
<220> FEATURE:
<223> OTHER INFORMATION: primer

<400> SEQUENCE: 31
gaatttcgcg cgcttggcgc gtgtaaccaa ctctgtgatt a                          41

<210> SEQ ID NO 32
<211> LENGTH: 41
<212> TYPE: DNA
<213> ORGANISM: Artificial Sequence
<220> FEATURE:
<223> OTHER INFORMATION: primer

<400> SEQUENCE: 32
taatcacaga gttggttaca cgcgccaagc gcgcgaaatt c                          41

<210> SEQ ID NO 33
<211> LENGTH: 41
<212> TYPE: DNA
<213> ORGANISM: Artificial Sequence
<220> FEATURE:
<223> OTHER INFORMATION: primer

<400> SEQUENCE: 33
tttcgcgcgc ttggcgctgg cgaccaactc tgtgattatc c                          41

<210> SEQ ID NO 34
<211> LENGTH: 41
<212> TYPE: DNA
<213> ORGANISM: Artificial Sequence
<220> FEATURE:
<223> OTHER INFORMATION: primer

<400> SEQUENCE: 34
ggataatcac agagttggtc gccagcgcca agcgcgcgaa a                          41

<210> SEQ ID NO 35
<211> LENGTH: 41
<212> TYPE: DNA
<213> ORGANISM: Artificial Sequence
<220> FEATURE:
<223> OTHER INFORMATION: primer

<400> SEQUENCE: 35
tgacctgttg gaattaagcg gcttgccgga cgaagctcgc a                          41

<210> SEQ ID NO 36
<211> LENGTH: 41
<212> TYPE: DNA
<213> ORGANISM: Artificial Sequence
<220> FEATURE:
<223> OTHER INFORMATION: primer

<400> SEQUENCE: 36
tgcgagcttc gtccggcaag ccgcttaatt ccaacaggtc a                          41

<210> SEQ ID NO 37
<211> LENGTH: 41
<212> TYPE: DNA
<213> ORGANISM: Artificial Sequence
<220> FEATURE:

```
<223> OTHER INFORMATION: primer

<400> SEQUENCE: 37
gctggcgacc aatgataacg ctttcttcaa cgaggacaac g                41

<210> SEQ ID NO 38
<211> LENGTH: 41
<212> TYPE: DNA
<213> ORGANISM: Artificial Sequence
<220> FEATURE:
<223> OTHER INFORMATION: primer

<400> SEQUENCE: 38
cgttgtcctc gttgaagaaa gcgttatcat tggtcgccag c                41

<210> SEQ ID NO 39
<211> LENGTH: 41
<212> TYPE: DNA
<213> ORGANISM: Artificial Sequence
<220> FEATURE:
<223> OTHER INFORMATION: primer

<400> SEQUENCE: 39
cgcaagcact acaccctgga gcgcagcgca taaccccta g                 41

<210> SEQ ID NO 40
<211> LENGTH: 41
<212> TYPE: DNA
<213> ORGANISM: Artificial Sequence
<220> FEATURE:
<223> OTHER INFORMATION: primer

<400> SEQUENCE: 40 ctaggggtt atgcgctgcg ctccagggtg tagtgcttgc g                 41
```

METHOD FOR PRODUCING HYDROXY-L-PIPECOLIC ACID

The present application is a Divisional of U.S. application Ser. No. 15/765,148, which is a National Stage of International Patent Application No. PCT/JP2016/079123, filed Sep. 30, 2016, which claims priority to Japanese Application No. 2015-197231, filed Oct. 2, 2015. The disclosure of each of the above identified applications is expressly incorporated by reference herein in its entirety.

TECHNICAL FIELD

The present invention relates to a method of biologically producing hydroxy-L-pipecolic acids, particularly to a method of producing hydroxy-L-pipecolic acids from L-pipecolic acid based on the use of enzymes that have the ability to produce the hydroxy-L-pipecolic acids.

BACKGROUND ART

Hydroxy-L-pipecolic acids are compounds useful as intermediates to produce pharmaceuticals, and the like. It is known that, for example, (4S)-hydroxy-L-pipecolic acid and (4R)-hydroxy-L-pipecolic acid can be used as precursors of a Rho kinase inhibitor (Patent Document 1) and the HIV protease inhibitor palinavir (Non-Patent Document 1), respectively, while (5S)-hydroxy-L-pipecolic acid and (5R)-hydroxy-L-pipecolic acid can be used as precursors of antimicrobials (Patent Document 2).

It has been known that hydroxy-L-pipecolic acids can be produced from L-pipecolic acid by biological approaches. Examples of proteins having the ability to convert L-pipecolic acid to (5S)-hydroxy-L-pipecolic acid reportedly include the BAB52605 protein derived from the root nodule bacterium *Mesorhizobium loti* strain MAFF303099 isolated from *Lotus japonicus*, the CAC47686 protein derived from the root nodule bacterium *Sinorhizobium meliloti* strain 1021 isolated from *Medicago sativa* (hereinafter sometimes referred to as "SmPH"), and a protein encoded in a polynucleotide (cistronic gene), the expression of which is initiated 48 nucleotides (corresponding to 16 amino acids) upstream of the translation start site described in the annotation of the EFV12517 protein derived from the *Segniliparus rugosus* strain ATCC BAA-974 (hereinafter sometimes referred to as "SruPH"), and the like (Patent Document 3). These hydroxylases can be used to convert L-pipecolic acid to hydroxy-L-pipecolic acids.

However, any of these hydroxylases also has the ability to produce hydroxy-L-proline through the hydroxylation of L-proline.

An L-pipecolic acid biologically produced by using an enzyme, microbial bodies, or the like may be contaminated with a trace amount of L-proline, for example, as a carry-over component from a medium used for the preparation of the enzyme or the microbial bodies.

Moreover, in cases where hydroxy-L-pipecolic acids are produced from pure L-pipecolic acid as a base material by using the hydroxylases, the hydroxylases to be used may be contaminated with L-proline.

Furthermore, even if neither L-pipecolic acid as a base material nor the hydroxylases are contaminated with L-proline, in cases where the hydroxylation reaction is achieved by culturing microbial bodies capable of expressing the hydroxylases, L-proline may potentially be produced as a by-product by those microbial bodies during the course of their growth.

Since the physicochemical properties of L-proline are close to those of L-pipecolic acid, it is difficult to obtain pure L-pipecolic acid with complete removal of L-proline.

Moreover, when L-pipecolic acid contaminated with L-proline is used as a base material along with any of the aforementioned enzymes in the conversion of L-pipecolic acid to a hydroxy-L-pipecolic acid, L-proline is converted to hydroxy-L-proline and, therefore, the resulting product will be a mixture of the hydroxy-L-pipecolic acid and hydroxy-L-proline, which makes it difficult to obtain the hydroxy-L-pipecolic acid of high purity. Also, since the physicochemical properties of hydroxy-L-proline are close to those of hydroxy-L-pipecolic acids, it is difficult to separate them from each other.

Accordingly, disadvantageously, a heavy burden in purification process and a huge expense of time and money have been required for the preparation of high-purity hydroxy-L-pipecolic acids with removal of hydroxy-L-proline because multiply repeated purification and use of expensive purification measures are required.

PRIOR ART DOCUMENTS

Patent Documents

Patent Document 1: JP-T-2010-514720
Patent Document 2: JP-T-2004-505088
Patent Document 3: WO2013/187438

Non-Patent Document

Non-Patent Document 1: Gillard el al., The Journal of Organic Chemistry, 1996, Vol. 61, pp. 2226

SUMMARY OF THE INVENTION

Technical Problem

As described above, methods of biologically producing hydroxy-L-pipecolic acids from L-pipecolic acid are known; however, any of those conventional methods is unsatisfactory as a production method for hydroxy-L-pipecolic acids of high purity, which are used as intermediates of pharmaceuticals, and the like, because not only hydroxy-L-pipecolic acids but also hydroxy-L-proline are produced by those methods. Accordingly, there is a demand for a more efficient production method.

Namely, an object of the present invention is to provide a novel method of producing high-purity hydroxy-L-pipecolic acids in an efficient and inexpensive manner while suppressing the production of hydroxy-L-proline.

Solution to Problem

The inventors intensively studied to solve the above-described problem and consequently found that particular pipecolic acid hydroxylases have the ability to convert L-pipecolic acid to hydroxy-L-pipecolic acids (L-pipecolic acid hydroxylation activity) in a 2-oxoglutarate-dependent fashion and have almost no activity to convert L-proline to hydroxy-L-proline (L-proline hydroxylation activity), and that various hydroxy-L-pipecolic acids with high optical purity can be obtained in a highly efficient manner by allowing those particular enzymes to act on L-pipecolic acid. The present invention was achieved based on these findings.

Now, the spirit of the present invention will be described below.

[1] A method of producing a hydroxy-L-pipecolic acid, the method comprising:

allowing an L-pipecolic acid hydroxylase, a microorganism or cell having the ability to produce the enzyme, a processed product of the microorganism or cell, and/or a culture liquid comprising the enzyme and obtained by culturing the microorganism or cell, to act on L-pipecolic acid as a substrate in the presence of 2-oxoglutaric acid and ferrous ion, wherein the L-pipecolic acid hydroxylase has the properties (1) and (2) below:

(1) the enzyme can act on L-pipecolic acid in the presence of 2-oxoglutaric acid and ferrous ion to add a hydroxy group to the carbon atom at positions 3, 4, and/or 5 of L-pipecolic acid; and (2) the enzyme has a catalytic efficiency (kcat/Km) with L-proline that is equal to or less than 7 times the catalytic efficiency (kcat/Km) with L-pipecolic acid.

[2] The method of producing a hydroxy-L-pipecolic acid according to [1], further comprising:

allowing L-lysine and/or DL-lysine to react with (i-1) one or more enzymes selected from the group consisting of an L-amino acid oxidase, an L-amino acid dehydrogenase and an L-amino acid aminotransferase, or (i-2) an amino acid racemase and one or more enzymes selected from the group consisting of a D-amino acid oxidase, a D-amino acid dehydrogenase and a D-amino acid aminotransferase, for the production of 3,4,5,6-tetrahydropyridine-2-carboxylic acid; and subsequently allowing an N-methyl-L-amino acid dehydrogenase to act on the 3,4,5,6-tetrahydropyridine-2-carboxylic acid for the production of the L-pipecolic acid as the substrate.

[3] The method of producing a hydroxy-L-pipecolic acid according to [1], further comprising:

allowing L-lysine to react with one or more enzymes selected from the group consisting of an L-lysine 6-oxidase, an L-lysine 6-dehydrogenase and an L-lysine 6-aminotransferase, for the production of 2,3,4,5-tetrahydropyridine-2-carboxylic acid; and subsequently allowing a pyrroline-5-carboxylate reductase to act on the 2,3,4,5-tetrahydropyridine-2-carboxylic acid for the production of the L-pipecolic acid as the substrate.

[4] The method of producing a hydroxy-L-pipecolic acid according to [1], further comprising allowing a lysine cyclodeaminase to act on L-lysine for the production of the L-pipecolic acid as the substrate.

[5] The method of producing a hydroxy-L-pipecolic acid according to any of [1] to [4], wherein the content of L-proline in the L-pipecolic acid as the substrate is not more than 10% (w/w).

[6] The method of producing a hydroxy-L-pipecolic acid according to any of [1] to [5], wherein the L-pipecolic acid hydroxylase further has the property (3) below:

(3) the microorganism or cell having the ability to produce the L-pipecolic acid hydroxylase, or the processed product of the microorganism or cell has a hydroxy-L-proline-producing activity that is not more than 55%, where a ratio of 100/corresponds to the hydroxy-L-pipecolic acid-producing activity of the same microorganism or cell, or of the same processed product.

[7] The method of producing a hydroxy-L-pipecolic acid according to any of [1] to [6], wherein the L-pipecolic acid hydroxylase comprises the protein (A), (B), or (C) below:

(A) a protein having an amino acid sequence represented by SEQ ID NO: 2, 12, 14, 16, 18, or 20;

(B) a protein having the same amino acid sequence as the amino acid sequence represented by SEQ ID NO: 2, 12, 14, 16, 18, or 20 except that one or several amino acids are deleted, substituted, inserted, and/or added, which protein has the aforementioned properties (1) and (2);

(C) a protein having an amino acid sequence with an identity of not less than 80% to the amino acid sequence represented by SEQ ID NO: 2, 12, 14, 16, 18, or 20, which protein has the aforementioned properties (1) and (2).

[8] The method of producing a hydroxy-L-pipecolic acid according to any of [1] to [7], wherein the microorganiam or cell having the ability to produce the L-pipecolic acid hydroxylase is a microorganism or cell transformed with DNA encoding the L-pipecolic acid hydroxylase.

[9] The method of producing a hydroxy-L-pipecolic acid according to [8], wherein the DNA encoding the L-pipecolic acid hydroxylase comprises the DNA (D), (E), or (F) below:

(D) DNA having a nucleotide sequence represented by SEQ ID NO: 1, 11, 13, 15, 17, or 19;

(E) DNA comprising the same nucleotide sequence as the nucleotide sequence represented by SEQ ID NO: 1, 11, 13, 15, 17, or 19 except that one or several bases are deleted, substituted, inserted, and/or added, which DNA encodes a protein having the aforementioned properties (1) and (2);

(F) DNA comprising a nucleotide sequence which hybridizes with a complementary strand of the nucleotide sequence represented by SEQ ID NO: 1, 11, 13, 15, 17, or 19 under stringent conditions, which DNA encodes a protein having the aforementioned properties (1) and (2).

Advantageous Effects of the Invention

According to the present invention, high-purity hydroxy-L-pipecolic acids with high optical purity can be produced in a highly efficient manner. In particular, according to the present invention, high-purity hydroxy-L-pipecolic acids can be produced even in cases where the L-pipecolic acid as the substrate is contaminated with L-proline.

Furthermore, the present invention is preferable from an industrial viewpoint because the production of hydroxy-L-proline can be reduced and, thus, high-purity hydroxy-L-pipecolic acids available as intermediates for pharmaceuticals, and the like can be produced at low cost and at less expense.

DESCRIPTION OF THE EMBODIMENTS

Figure 1:
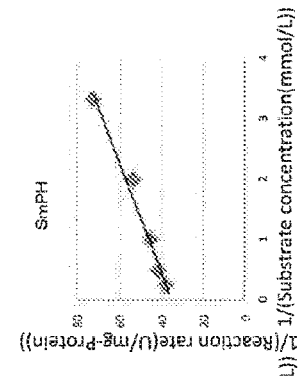
FIG. 1 represents graphs obtained in Example 3 by plotting the reciprocals of the respective concentrations of L-pipecolic acid (mmol/L) on the x-axis and the reciprocals of the hydroxy-L-pipecolic acid-producing activities per milligram of each hydroxylase (U/mg) at the respective concentrations of L-pipecolic acid on the y-axis.
Figure 1:
Figure 1:
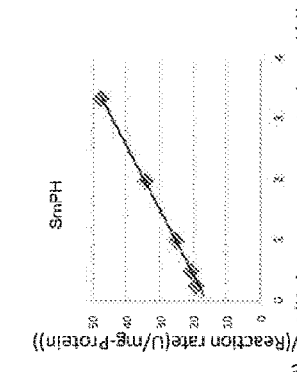
Figure 1:
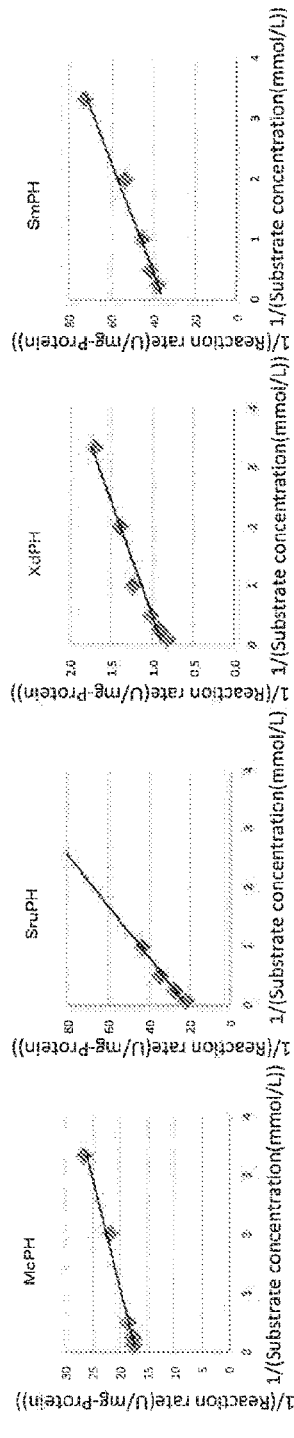
Figure 1:
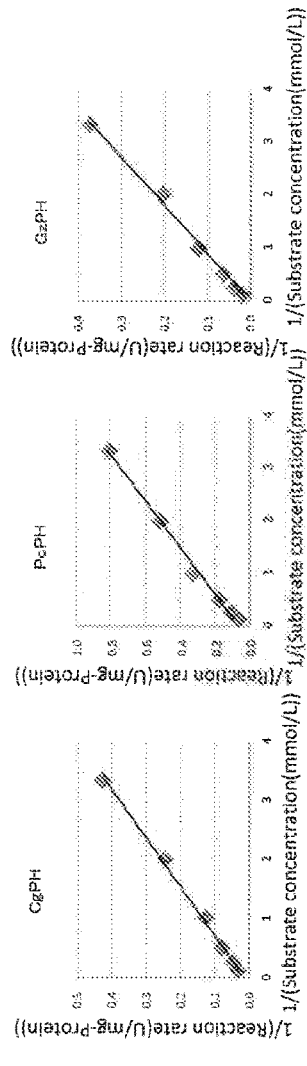
Figure 1:
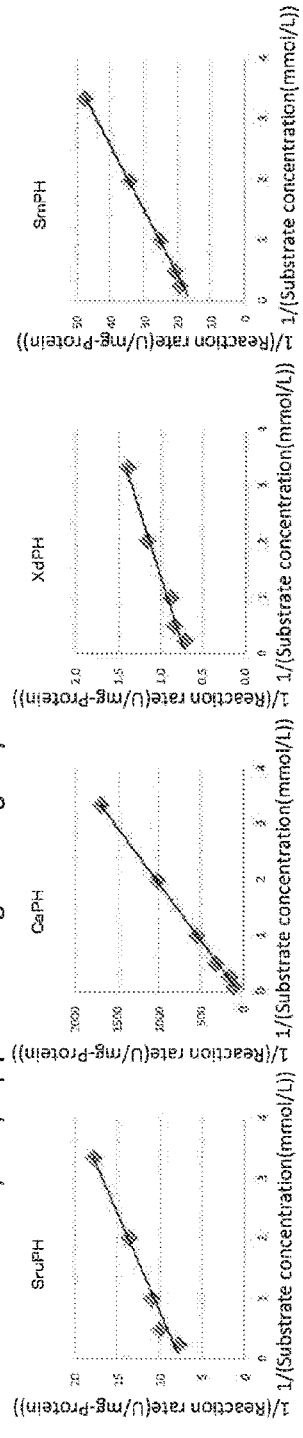

Now, the present invention will be described below in detail.

In the present specification, the "L-pipecolic acid hydroxylation activity" means the ability to add a hydroxy group to the carbon atom at positions 3, 4, and/or 5 of L-pipecolic acid.

Whether or not the "L-pipecolic acid hydroxylation activity" is retained in a measurement subject can be confirmed, for example, by allowing an enzyme, which is a measurement subject, to act on L-pipecolic acid in a reaction system containing L-pipecolic acid as a substrate and further containing 2-oxoglutaric acid and ferrous ion, and then measuring the amount of resulting hydroxy-L-pipecolic acid.

The term "enzyme" in the present specification includes a purified enzyme (including a partially purified enzyme), and an immobilized enzyme on a carrier prepared by using a conventional immobilization technique, including, for example, an enzyme immobilized on a carrier such as polyacrylamide and carrageenan gels, and the like.

In the present specification, the term "expression vector" refers to a genetic element that is used for the introduction of a polynucleotide encoding a protein with a desired function into a host organism to be recombined, followed by the replication of the polynucleotide and the expression of the protein with the desired function in the host organism. Examples of the expression vector include, but are not limited to, plasmid, virus, phage, cosmid, and the like, and a preferable example is plasmid.

In the present specification, "transformant" means a microorganism or cell into which a gene of interest has been introduced using an expression vector, such as those as described above, to allow the microorganism or cell to exhibit a desired phenotype associated with an encoded protein with a desired function.

The method of producing a hydroxy-L-pipecolic acid according to the present invention is characterized by allowing an L-pipecolic acid hydroxylase, a microorganism or cell having the ability to produce the enzyme, a processed product of the microorganism or cell, and/or a culture liquid comprising the enzyme and obtained by culturing the microorganism or cell, to act on the L-pipecolic acid as the substrate in the presence of 2-oxoglutaric acid and ferrous ion, wherein the L-pipecolic acid hydroxylase has the properties (1) and (2) below:

(1) the enzyme can act on L-pipecolic acid in the presence of 2-oxoglutaric acid and ferrous ion to add a hydroxy group to the carbon atom at positions 3, 4, and/or 5 of L-pipecolic acid; and (2) the enzyme has a catalytic efficiency (kcat/Km) with L-proline that is equal to, or less than 7 times the catalytic efficiency (kcat/Km) with L-pipecolic acid.

The L-pipecolic acid hydroxylase used in the present invention (hereinafter sometimes referred to as "L-pipecolic acid hydroxylase of the present invention") is an enzyme capable of acting on L-pipecolic acid in the presence of 2-oxoglutaric acid and ferrous ion to add a hydroxy group to the carbon atom at positions 3, 4, and/or 5 of L-pipecolic acid.

The amount of 2-oxoglutaric acid is not particularly limited as long as it is not an amount so as to inhibit the reaction, but it is normally an amount equimolar to or greater than the amount of L-pipecolic acid in the reaction system and is preferably an amount ranging from 1 to 1.2 times the number of moles of L-pipecolic acid in the reaction system.

The amount of ferrous ion is not particularly limited as long as it is not an amount so as to inhibit the reaction, but it normally from 0.000 to 0.5 mol, preferably from 0.001 to 0.1 mol, per mol of L-pipecolic acid in the reaction system.

The addition of, for example, ferrous sulfate, ferrous chloride, ferrous citrate, and the like allows ferrous ions to exist in the reaction system.

The L-pipecolic acid hydroxylase of the present invention preferably includes a protein having an amino acid sequence represented by SEQ ID NO: 2, 12, 14, 16, 18, or 20.

Moreover, the L-pipecolic acid hydroxylase of the present invention may include a protein having an amino acid sequence homologous to the amino acid sequence represented by SEQ ID NO: 2, 12, 14, 16, 18, or 20, which is a protein having the L-pipecolic acid hydroxylation activity and the properties (1) and (2) as described above.

Such a protein having an amino acid sequence homologous to the amino acid sequence represented by SEQ ID NO: 2, 12, 14, 16, 18, or 20 includes a protein having the same amino acid sequence as the amino acid sequence represented by SEQ ID NO: 2, 12, 14, 16, 18, or 20 except that one or several amino acids are deleted, substituted, inserted, and/or added. In the case of substitution, insertion, or addition, conservative mutations resulting from conservative substitution, insertion, or addition of one or several amino acids are preferable.

The phrase "one or several amino acids" herein means usually 1 to 100, preferably 1 to 50, more preferably 1 to 20, still more preferably 1 to 10, particularly preferably 1 to 5, amino acids.

Moreover, the protein having an amino acid sequence homologous to the amino acid sequence represented by SEQ ID NO: 2, 12, 14, 16, 18, or 20 includes a protein having an amino acid sequence with an identity of not less than 70% to the amino acid sequence represented by SEQ ID NO: 2, 12, 14, 16, 18, or 20 in its full-length form. The protein includes a protein having an amino acid sequence with an identity of preferably not less than 80%, more preferably not less than 90%, and still more preferably not less than 95% to the above-described amino acid sequence in its full-length form.

In the present invention, the term "sequence identity" means, in nucleotide sequences or amino acid sequences, the percentage of identical nucleotides or amino acids shared between two sequences, which percentage is determined by aligning those two sequences in an optimal pairwise alignment. That is, the identity can be calculated with the formula below and can be calculated by using a commercially available algorithm:

Identity=(the number of matches at each position/the total number of positions)×100.

Moreover, such algorithms are incorporated in NBLAST and XBLAST programs as described in Altschul et al., J. Mol. Biol. 215 (1990) pp. 403-410. More particularly, the identity search and the identity analysis can be performed on nucleotide sequences or amino acid sequences by means of algorithms or programs well known to those skilled in the art (for example, BLASTN, BLASTP, BLASTX, ClustalW). Parameters for use with a program can be appropriately set by those skilled in the art and default parameters for each program may also be used. Specific procedures in those analysis methods are well known to those skilled in the art.

The amino acid sequences represented by SEQ ID NO: 2, 12, 14, 16, and 18 are based on the genome information of *Micromonospora chokoriensis*, the *Colletotrichum gloeosporioides* strain Nara qc5, the *Penicillium chrysogenum* strain Wisconsin 54-1255, the *Gibberella zeae* strain PH-1, and a *Kordia jejudnensis* strain, respectively.

Among those L-pipecolic acid hydroxylases of the present invention, the protein having the amino acid sequence represented by SEQ ID NO: 2, 18, or 20, and the protein having an amino acid sequence homologous to the amino acid sequence represented by SEQ ID NO: 2, 18, or 20 and having the L-pipecolic acid hydroxylation activity selectively hydroxylates the carbon atom at position 5 of L-pipecolic acid and therefore they can produce (5S)-hydroxy-L-pipecolic acid with high efficiency.

Among those L-pipecolic acid hydroxylases of the present invention, the protein having the amino acid sequence represented by SEQ ID NO: 12, 14, or 16, and the protein having an amino acid sequence homologous to the amino acid sequence represented by SEQ ID NO: 12, 14, or 16 and having the L-pipecolic acid hydroxylation activity selectively hydroxylates the carbon atom at position 4 of L-pipecolic acid and therefore they can produce (4S)-hydroxy-L-pipecolic acid with high efficiency.

In the present invention, one, two or more types of L-pipecolic acid hydroxylases can be used.

The L-pipecolic acid hydroxylase of the present invention can be obtained by purification from *Micromonospora chokoriensis*, the *Colletotrichum gloeosporioides* strain Nara qc5, the *Penicillium chrysogenum* strain Wisconsin 54-1255, the *Gibberela zeae* strain PH-1, the *Kordia jejudonensis* strain, or the like.

Also, the L-pipecolic acid hydroxylase of the present invention can be obtained by cloning a DNA encoding the L-pipecolic acid hydroxylase of the present invention by means of known methods including PCR (polymerase chain reaction), hybridization, and the like, and then allowing the L-pipecolic acid hydroxylase to be expressed in an appropriate host.

The DNAs encoding L-pipecolic acid hydroxylases comprising the proteins having the amino acid sequences represented by SEQ ID NO: 2, 12, 14, 16, 18, and 20 respectively correspond to, for example, DNAs comprising the nucleotide sequences represented by SEQ ID NO: 1, 11, 13, 15, 17, and 19. Moreover, the DNA may be a DNA homologous to the above DNA comprising the nucleotide sequence represented by SEQ ID NO: 1, 11, 13, 15, 17, or 19, which encodes a protein having the L-pipecolic acid hydroxylation activity and the properties (1) and (2) as described above.

Such a DNA homologous to the above DNA comprising the nucleotide sequence represented by SEQ ID NO: 1, 11, 13, 15, 17, or 19 includes a DNA comprising the same nucleotide sequence as the nucleotide sequence represented by SEQ ID NO: 1, 11, 13, 15, 17, or 19 except that one or several bases are deleted, substituted, inserted, and/or added. In the case of substitution, insertion, or addition, conservative mutations resulting from conservative substitution, insertion, or addition of one or several bases are preferable.

The phrase "one or several bases" herein means usually 1 to 300, preferably 1 to 150, more preferably 1 to 60, still more preferably 1 to 30, more preferably 1 to 15, particularly preferably 1 to 10, bases.

The nucleotide sequences represented by SEQ ID NO: 1, 11, 13, 15, and 17 respectively correspond to the nucleotide sequences of genes originated from *Micromonospora chokoriensis*, the *Colletotrichum gloeosporioides* strain Nara qc5, the *Penicillium chrysogenum* strain Wisconsin 54-1255, the *Gibberella zeae* strain PH-1, and the *Kordia jejudonensis* strain, which nucleotide sequences are codon-optimized for *E. coli* expression and encode the amino acid sequences represented by SEQ ID NO: 2, 12, 14, 16, and 18. Such a DNA with codon-optimization according to the host for transformation is, of course, included in examples of the DNA encoding the L-pipecolic acid hydroxylase of the present invention.

Moreover, the DNA homologous to the above DNA comprising the nucleotide sequence represented by SEQ ID NO: 1, 11, 13, 15, 17, or 19 may be a DNA comprising a nucleotide sequence which hybridizes with the complementary strand of the nucleotide sequence represented by SEQ ID NO: 1, 11, 13, 15, 17, or 19 under stringent conditions.

The phrase "nucleotide sequence which hybridizes under stringent conditions" herein means the nucleotide sequence of a DNA that is obtained by using a DNA probe and using colony hybridization, plaque hybridization, Southern blot hybridization, or the like under stringent conditions.

Examples of the stringent conditions include, in cases of colony hybridization or plaque hybridization, conditions where filters with immobilized DNA from colonies or plaques, or with immobilized DNA fragments thereof are used to perform hybridization at 65° C. in the presence of 0.7 mol/L to 1 mol/L aqueous solution of sodium chloride, and the filters are subsequently washed under a temperature condition of 65° C. by using 0.1×SSC solution (the composition of 1×SSC: 150 mmol/L aqueous solution of sodium chloride, 15 mmol/L aqueous solution of sodium citrate). Such hybridization can be performed in accordance with the methods described in Molecular Cloning: A laboratory Manual, $2^d$ Ed., Cold Spring Harbor Laboratory, Cold Spring Harbor, N.Y., 1989, and the like.

Those skilled in the art will be able to introduce a desired mutation into the DNA comprising the nucleotide sequence represented by SEQ ID NO: 1, 11, 13, 15, 17, or 19 by deletion, substitution, insertion, and/or addition of one or more bases by means of site-directed mutagenesis (Nucleic Acids Res. 10, pp. 6487 (1982); Methods in Enzymol. 100, pp. 448 (1983); Molecular Cloning; PCR: A Practical Approach, IRL Press, pp. 200 (1991)) and the like to provide a mutant DNA of the DNA comprising the nucleotide sequence represented by SEQ ID NO: 1, 11, 13, 15, 17, or 19.

Moreover, the amino acid information of the L-pipecolic acid hydroxylase of the present invention or the nucleotide sequence information of a DNA encoding the same may be obtained by a homology search of the entire or part of the amino acid sequence represented by SEQ ID NO: 2, 12, 14, 16, 18, or 20, or the entire or part of the nucleotide sequence represented by SEQ ID NO: 1, 11, 13, 15, 17, or 19, against databases such as DNA Databank of JAPAN (DDBJ).

Moreover, the L-pipecolic acid hydroxylase of the present invention has a catalytic efficiency (kcat/Km) with L-proline that is equal to, or less than 7 times, preferably equal to, or less than 2 times, more preferably equal to, or less than 1 time, still more preferably equal to, or less than 0.5 times, and particularly preferably equal to, or less than 0.1 times the catalytic efficiency (kcat/Km) with L-pipecolic acid. An L-pipecolic acid hydroxylase exhibiting virtually no hydroxy-L-proline-producing activity is most preferable. The phrase "virtually no hydroxy-L-proline-producing activity" in the present invention does not mean not producing even one molecule of hydroxy-L-proline but means producing an undetectable amount of, or a detectable but trace amount of hydroxy-L-proline, which is almost a negligible amount based on the common knowledge of those skilled in the art.

The catalytic efficiency (kcat/Km) in the present invention can be determined, for example, by a method using the Michaelis-Menten kinetic equation to calculate the kcat/Km value. Herein, the term "kcat" refers to the catalytic efficiency per molecule of an enzyme, while the term "Km" is an index representing the affinity of the enzyme with its substrate.

A specific method to calculate Km and kcat is as described below. First, the hydroxy-L-pipecolic acid-producing activity per milligram of each hydroxylase (U/mg) at each concentration of L-pipecolic acid is measured in a particular range of substrate concentration. One unit (U) herein represents the ability to produce 1 mol of a hydroxy-L-pipecolic acid in the period of 1 minute. Subsequently, the reciprocals of the respective concentrations of L-pipecolic acid (mmol/L) and the reciprocals of the hydroxy-L-pipecolic acid-producing activities per milligram of the hydroxylase (U/mg) at the respective concentrations of L-pipecolic acid are plotted on the x-axis and the y-axis, respectively. It is known that, in those linear plots, the reciprocal of each intercept with the x-axis, multiplied with −1, represents a km value (mmol/L) and the reciprocal of each intercept with the y-axis represents a Vmax value (U/mg), the maximum rate of reaction. The catalytic ability per molecule of the enzyme (kcat) can be calculated from the Vmax and the molecular weight of the enzyme. The thus-obtained kcat and km values can be used to calculate the catalytic efficiency (kcat/Km), which is an index representing the catalytic ability of the enzyme.

As an enzyme to be used for the calculation of the catalytic efficiency, a crudely or finely purified material containing an enzyme fraction extracted from the microorganism or cell having the ability to produce the enzyme, which are disrupted by treatment with an organic solvent, a surfactant, and the like, and/or by physical or enzymatic treatment, can be used. The level of the enzymatic activity and the reaction time can be set as desired to the extent that the enzymatic activity is increased proportionally to the amount of the reaction time.

Details of the Michaelis-Menten equation and the like are described in, for example, "Biochemical Research Methods, Vol. 21: Guide to Experiments on Enzymatic Reaction Kinetics, Gakkai Shuppan Center, Ltd." and the like.

Furthermore, the L-pipecolic acid hydroxylase activity in the present invention may also be simply evaluated by the following procedures.

The microorganism or cell having the ability to produce the L-pipecolic acid hydroxylase of the present invention, or the processed product of the microorganism or cell is allowed to react with L-pipecolic acid or L-proline and then the hydroxy-L-pipecolic acid-producing activity (U/g) and the hydroxy-L-proline-producing activity (U/g) per amount of inputted cells (unit: gram (g) or turbidity) or per mass of total proteins (unit: g) are measured in particular substrate concentrations. Then, the activity to produce hydroxy-L-proline from L-proline at a particular substrate concentration (relative value) is calculated, where a ratio of 100% corresponds to the activity to produce a hydroxy-L-pipecolic acid from L-pipecolic acid at the same substrate concentration.

As for the L-pipecolic acid hydroxylase of the present invention, the activity to produce hydroxy-L-proline in the microorganism or cell having the ability to produce the L-pipecolic acid hydroxylase, or in the processed product of the microorganism or cell is normally not more than 55%, preferably not more than 50%, more preferably not more than 35%, particularly preferably not more than 20%, and most preferably 0% relative, where a ratio of 100% corresponds to the activity to produce a hydroxy-L-pipecolic acid in the microorganism or cell having the ability to produce the enzyme, or in the processed product of the microorganism or cell.

Because the L-pipecolic acid hydroxylase used in the present invention (hereinafter sometimes referred to as "L-pipecolic acid hydroxylase of the present invention") can hydroxylate L-pipecolic acid with high regiospecificity and high stereospecificity, hydroxy-L-pipecolic acids with high optical purity can be obtained with high efficiency.

In the method of producing a hydroxy-L-pipecolic acid according to the present invention, the L-pipecolic acid hydroxylase of the present invention may be directly used for the reaction, or a microorganism or cell having the ability to produce the enzyme, a processed product of the microorganism or cell, and/or a culture liquid comprising the enzyme and obtained by culturing the microorganism or cell may be used for the reaction.

The microorganism or cell having the ability to produce the L-pipecolic acid hydroxylase of the present invention may be a microorganism or cell inherently having the above production ability, or a microorganism or cell on which the above production ability has been conferred by breeding. Moreover, the microorganism or cell having the ability to produce the L-pipecolic acid hydroxylase of the present invention is not limited to a living microorganism or cell but includes those apparently dead as living bodies and retaining the ability of the enzyme.

Moreover, the types of microorganisms or cells having the ability to produce an L-pipecolic acid hydroxylase include those described below as "host microorganisms" or "host cells".

Known methods such as recombinant gene technology (transformation) and mutagenesis may be employed as the means to impart the above production ability by breeding. Several different methods may be used as the method of transformation, in which the expression of a gene of interest on DNA is enhanced by introducing DNA carrying the gene of interest, by modifying an expression regulatory sequence of the gene, such as a promoter, on the chromosome, or the like.

Among them, it is preferred to use a microorganism or cell which has been transformed with a DNA encoding the L-pipecolic acid hydroxylase of the present invention.

For example, a DNA encoding the L-pipecolic acid hydroxylase of the present invention is operatively inserted into a known expression vector to construct an L-pipecolic acid hydroxylase-expressing vector, and the expression vector is used to transform a host cell. Thus, a transformant into which the DNA encoding the L-pipecolic acid hydroxylase of the present invention has been introduced can be produced.

Moreover, the transformant can also be produced by incorporation of the DNA encoding the L-pipecolic acid hydroxylase of the present invention into a chromosome of the host cell in such a way that expression of the enzyme is possible, which incorporation is mediated by a procedure such as homologous recombination or the like.

The procedure for establishing the transformant, the method of constructing a recombinant vector suitable for the host, and the method of culturing the host can be carried out in accordance with techniques conventionally used in the fields of molecular biology, bioengineering and genetic engineering (for example, methods described in Molecular Cloning, supra).

Examples of the method of preparing the transformant include a method in which the DNA encoding the L-pipecolic acid hydroxylase of the present invention is introduced into a plasmid vector, phage vector, or virus vector that stably exists in a host cell and then the constructed expression vector is introduced into the host cell, or a method in which the DNA is directly introduced into the host genome, in both of which methods the genetic information on the DNA is then transcribed and translated.

In this process, it is preferable to link a promoter to the DNA on the 5'-upstream side and it is more preferable to further link a terminator to the DNA on the 3'-downstream side, which promoter and terminator are suitable in the host. As long as the promoter and the terminator are a promoter and a terminator which are known to be functional in a host, they can be used and are not particularly limited. For example, vectors, promoters, and terminators described in "Fundamental Microbiology 8: Genetic Engineering, Kyoritsu Shuppan Co., Ltd." can be used.

The host microorganism or host cell to be transformed is not particularly limited as long as the host itself does not adversely affect the reaction of L-pipecolic acid.

Examples of the host microorganism include prokaryotes such as *E. coli* (bacteria of the genus *Escherichia*), bacteria of the genus *Bacillus*, bacteria of the genus *Pseudomonas*, coryneform bacteria, root-nodule bacteria, bacteria of the genus *Lactobacillus*, bacteria of the genus *Brevibacillus*, bacteria of the genus *Anaerobiospirillum*, bacteria of the genus *Actinobacillus*, actinomycetes, and the like; and eukaryotes including fungi, such as yeasts and filamentous fungi, plants, animals, and the like. Among them, *E. coli*, yeasts, and coryneform bacteria are preferable, and *E. coli* is particularly preferable.

Examples of the host microorganism include microorganisms as described below:

bacteria belonging to the genera *Escherichia, Bacillus, Pseudmonas, Corynebacterium, Rhizobium, Lactobacillus, Brevibacillus, Anacrobiospirillum, Actinobacillus, Serraia, Brevibaclerium, Streptococcus*, and the like, whose host vector systems have been established;

actinomycetes belonging to the genera *Rhodococcus, Streptomyces*, and the like, whose host vector systems have been established;

yeasts belonging to the genera *Saccharomyces, Kluyveromyces, Schizosaccharomyces, Zygosaccharomyces, Yarrowia, Trichosporon, Rhodosporidium, Hansenula, Pichia, Candida*, and the like, whose host vector systems have been established; and fungi belonging to the genera *Neurspora, Aspergillus, Cephalosporium, Trichoderma*, and the like, whose host vector systems have been established.

Examples of preferable host microorganisms and of a preferable transformation procedure, vector, promoter, and terminator for each microorganism will be described below. However, the present invention is not limited thereto.

For the genus *Escherichia*, especially *Escherichia coli*, examples of the plasmid vector include plasmids of the pBR series, the pUC series, and the like; and examples of the promoter include lac (β-galactosidase), trp (tryptophan operon), lac, trc (a fusion of lac and trp), the PL and PR promoters of phage lambda, promoters derived from T7 phage, and the like. Moreover, examples of the terminator include terminators derived from trpA, phages, and rrnB ribosomal RNA, and the like. Among those promoters, a promoter that allows inducible gene expression may also be used for the purpose of improving the expression efficiency. For example, in the case of the above lac promoter, gene expression can be induced by addition of an inducer such as lactose or ispropyl-β-D-thiogalactoside (IPTG).

For the genus *Bacillus*, examples of the vector can include plasmids based on pUJB110, pC194, and the like, which may be integrated into a chromosome. As the promoter and the terminator, those of genes for enzymes, such as alkaline protease, neutral protease, and α-amylase, can be used.

For the genus *Pseudomonas*, examples of the vector can include generic host vector systems established in *Pseudomonas putida, Pseudomonas cepacia*, and the like; the wide-host-range vector pKT240 (containing genes required for autonomous replication and derived from RSF1010 and the like), which is based on a plasmid involved in degradation of toluene compounds, TOL plasmid (Gene, 26, 273-82 (1983)); and the like.

For the genus *Brevibacterium*, especially *Brevibacterium lactofermentum*, examples of the vector can include plasmid vectors such as pAJ43 (Gene, 39, 281 (1985)). As the promoter and the terminator, various promoters and terminators used in *E. coli* can be used.

For the genus *Corynebacterium*, especially *Corynebacterium glutamicum*, examples of the vector include plasmid vectors such as pCS11 (JP-57-183799 A) and pCB101 (Mol. Gen. Genet., 196, 175 (1984)).

For *Saccharomyces*, especially *Saccharomyces cerevisiae*, examples of the vector include plasmids of the YRp series, the YEp series, the YCp series, and the YIp series, and the like. Moreover, examples of promoters and terminators which may be used include those of the genes for various enzymes such as alcohol dehydrogenase, glyceraldehyde-3-phosphate dehydrogenase, acid phosphatase, i-galactosidase, phosphoglycerate kinase, and enolase.

For the genus *Schizosaccharomyces*, examples of the vector can include plasmid vectors, such as the plasmid vectors derived from *Schizosaccharomyces pombe* described in Mol. Cell. Biol., 6, 80 (1986). In particular, pAUR224 is commercially available from Takara Shuzo Co., Ltd. and readily available.

In the genus *Asperillus, Aspegillus niger, Aspergillus oryzae* and the like are the best-studied species among molds, in which plasmids and integration into the chromosome are applicable, and promoters for extracellularly secreted protease and amylase can be used (Trends in Biotechnology, 7, 283-287 (1989)).

Moreover, examples of the host cell include cells from animals, such as insects (for example, silkworm)(Nature, 315, 592-594 (1985)), and from plants such as rapeseed, maize, and potato. Also, cell-free protein synthesis system from *E. coli* cell-free extract, wheat germ and the like has been established and may preferably be used.

Moreover, various host vector systems other than the above-described systems have also been established, and those systems may be used as appropriate.

In the present specification, a "processed product of the microorganism or cell having the ability to produce an L-pipecolic acid hydroxylase" refers to a product that is prepared by culturing the microorganism or cell having the ability to produce an L-pipecolic acid hydroxylase, and then 1) treating the microorganism or cell with an organic solvent, surfactant, and the like, 2) freeze-drying the microorganism or cell, 3) immobilizing the microorganism or cell on a carrier and the like, 4) physically or enzymatically disrupting the microorganism or cell, or 5) separating an enzyme fraction as a crudely or finely purified material from any of the products of the aforementioned treatments 1) to 4).

Examples of the organic solvent include methanol, ethanol, 1-propanol, 2-propanol, 1-butanol, tert-butanol, acetone, dimethyl sulfoxide, ethyl acetate, butyl acetate, toluene, chloroform, n-hexane, and the like.

Examples of the surfactant include nonionic surfactants, such as Tween-20, Triton X-100, Brij 35, dodecyl-β-D-maltoside, Nonidet P-40, and octyl-β-D-glucoside; ampho-teric-ionic surfactants, such as 3-(3-cholamidopropyl)dimethylammonio-1-propanesulfonate (CHAPS); anionic surfactants, such as sodium dodecyl sulfate (SDS); and the like.

Specific examples of a procedure to immobilize the microorganism or cell on a carrier and the like include procedures to immobilize an enzyme fraction from the microorganism or cell on a carrier, and other procedures, where representative examples of the carrier include polyacrylamide gel, carrageenan gel, ion exchange resins, and the like.

Examples of a procedure to physically disrupt the microorganism or cell include sonication, high-pressure treatment with French Press, mechanical milling treatment using a homogenizer, Dyno-Mill bead mill, or the like, and other procedures.

Examples of a procedure to enzymatically disrupt the microorganism or cell include a procedure based on the treatment with an enzyme having the cell wall lysis activity, such as lysozyme or the like.

As a separation procedure in the enzyme purification, a conventional procedure for enzyme isolation and purification may be used. For example, a purified material can be separated from the extract prepared by any of the aforementioned procedures or the like, using each or a combination of centrifugation, ultrafiltration, salting-out with ammonium sulfate or the like, desalting, precipitation with an organic solvent, chromatography using various resins (anion exchange chromatography, cation exchange chromatography, hydrophobic chromatography, gel filtration, affinity chromatography), electrophoresis such as isoelectric focusing or the like, and the like.

Examples of the culture liquid comprising the L-pipecolic acid hydroxylase of the present invention and obtained by culturing the microorganism or cell having the ability to produce the enzyme include a suspension of the microorganism or cell and a liquid medium; and in cases where the microorganism or cell is a microorganism or cell for secretory expression, the supernatant obtained by removing the microorganism or cell by centrifugation and the like, and a concentrate of the supernatant; and the like.

In the present specification, a "culture liquid comprising the L-pipecolic acid hydroxylase and obtained by culturing the microorganism or cell having the ability to produce the enzyme" refers to 1) a culture liquid of the microorganism or cell, 2) a culture liquid obtained by treating the culture liquid of the microorganism or cell with an organic solvent, a surfactant, and the like, and 3) a culture liquid in which the cell membrane of the microorganism or cell has been physically or enzymatically disrupted.

As the organic solvent, surfactant, and the physical or enzymatic disruption method, the above-described materials and procedures can be used.

The method of producing a hydroxy-L-pipecolic acid according to the present invention is characterized by allowing an L-pipecolic acid hydroxylase, a microorganism or cell having the ability to produce the enzyme, a processed product of the microorganism or cell, and/or a culture liquid comprising the enzyme and obtained by culturing the microorganism or cell to act on the L-pipecolic acid as the substrate in the presence of 2-oxoglutaric acid and ferrous ion, and thereby producing a hydroxy-L-pipecolic acid.

In the present invention, as the L-pipecolic acid as the substrate, pure L-pipecolic acid may be used and L-pipecolic acid containing a trace amount of L-proline may also be used. The content of L-proline is normally not more than 10% (w/w), preferably not more than 1% (w/w), and particularly preferably not more than 0.1% (w/w).

Moreover, as the L-pipecolic acid as the substrate, a commercial L-pipecolic acid may be used and an L-pipecolic acid biologically produced by using an enzyme, microbial bodies, and the like may also be used. Biologically produced L-pipecolic acid may be contaminated with L-proline, for example, as a carry-over component from a medium used for the preparation of the enzyme or the microbial bodies; in the present invention, L-pipecolic acid can be contaminated with the above-described content of L-proline.

Examples of a method of biologically producing L-pipecolic acid include the methods as described below:

(i) allowing L-lysine and/or DL-lysine to react with (i-1) one or more enzymes selected from the group consisting of an L-amino acid oxidase, an L-amino acid dehydrogenase and an L-amino acid aminotransferase, or (i-2) an amino acid racemase and one or mom enzymes selected from the group consisting of a D-amino acid oxidase, a D-amino acid dehydrogenase and a D-amino acid aminotransferase, for the production of 3,4,5,6-tetrahydropyridine-2-carboxylic acid; and subsequently allowing an N-methyl-L-amino acid dehydrogenase to act on the 3,4,5,6-tetrahydropyridine-2-carboxylic acid for the production of L-pipecolic acid;

(ii) allowing L-lysine to react with one or more enzymes selected from the group consisting of an L-lysine 6-oxidase, an L-lysine 6-dehydrogenase and an L-lysine 6-aminotransferase, for the production of 2,3,4,5-tetrahydropyridine-2-carboxylic acid; and subsequently allowing a pyrroline-5-carboxylate reductase to act on the 2,3,4,5-tetrahydropyridine-2-carboxylic acid for the production of L-pipecolic acid; and (iii) allowing a lysine cyclodeaminase to act on L-lysine for the production of L-pipecolic acid.

The first method of producing L-pipecolic acid in the present invention is a production method as described below, the production method characterized by:

(i) allowing L-lysine and/or DL-lysine to react with (i-1) one or more enzymes selected from the group consisting of an L-amino acid oxidase, an L-amino acid dehydrogenase and an L-amino acid aminotransferase, or (i-2) an amino acid racemase and one or more enzymes selected from the group consisting of a D-amino acid oxidase, a D-amino acid dehydrogenase and a D-amino acid aminotransferase, for the production of 3,4,5,6-tetrahydropyridine-2-carboxylic acid; and subsequently allowing an N-methyl-L-amino acid dehydrogenase to act on the 3,4,5,6-tetrahydropyridine-2-carboxylic acid for the production of L-pipecolic acid.

The method will be described below by illustrating a scheme.

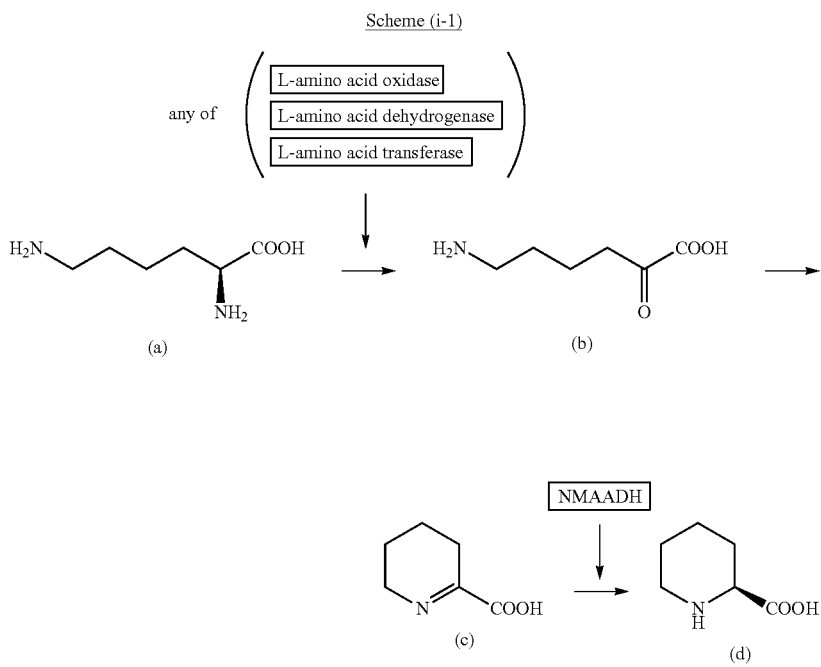

In Scheme (i-1), at least one enzyme selected from the group consisting of an L-amino acid oxidase, an L-amino acid dehydrogenase and an L-amino acid transferase, and an N-methyl-L-amino acid dehydrogenase (NMAADH) are used.

First, the compound (a) (L-lysine) is converted to the compound (b) by an enzyme selected from the group consisting of an L-amino acid oxidase, an L-amino acid dehydrogenase and an L-amino acid transferase. The compound (b) is spontaneously converted to the compound (c) (3,4,5,6-tetrahydropyridine-2-carboxylic acid). Then, the compound (c) is converted to the compound (d)(L-pipecolic acid) by an N-methyl-L-amino acid dehydrogenase (NMAADH, also known as DpkA).

Here, the L-amino acid oxidase is not particularly limited as long as it is an enzyme which can catalyze the substitution of the amino group at position 2 of L-lysine with an oxo group, but examples of the L-amino acid oxidase include a protein as described in J. Biochem., 2015, 157 (4), pp. 201, or proteins each having an amino acid sequence with an identity of not less than 80%, preferably not less than 90%, and more preferably not less than 95% to the amino acid sequence of the above protein and maintaining the activity thereof.

The L-amino acid dehydrogenase is not particularly limited as long as it is an enzyme which can catalyze the substitution of the amino group at position 2 of L-lysine with an oxo group, but examples of the L-amino acid dehydrogenase include a protein as described in Nature, 1%6, 211, pp. 854, or proteins each having an amino acid sequence with an identity of not less than 80%, preferably not less than 90%, and more preferably not less than 95% to the amino acid sequence of the above protein and maintaining the activity thereof.

The L-amino acid transferase (L-amino acid aminotransferase) is not particularly limited as long as it is an enzyme which can catalyze the substitution of the amino group at position 2 of L-lysine with an oxo group, but examples of the L-amino acid transferase include a protein containing an amino acid sequence as described in Eur. J. Biochem., 1998, 254, pp. 347, or proteins each having an amino acid sequence with an identity of not less than 80%, preferably not less than 90%, and more preferably not less than 95% to the amino acid sequence of the above protein and maintaining the activity thereof.

The N-methyl-1-amino acid dehydrogenase is not particularly limited as long as it is an enzyme which can catalyze the conversion of 3,4,5,6-tetrahydropyridine-2-carboxylic acid to L-pipecolic acid, but examples of the N-methyl-L-amino acid dehydrogenase include DpkA described in J. Biol. Chem. 2005, 280(49), pp. 40875, or proteins each having an amino acid sequence with an identity of not less than 80%, preferably not less than 90%, and more preferably not less than 95% to the amino acid sequence of DpkA and maintaining the activity thereof.

Scheme (I-2)

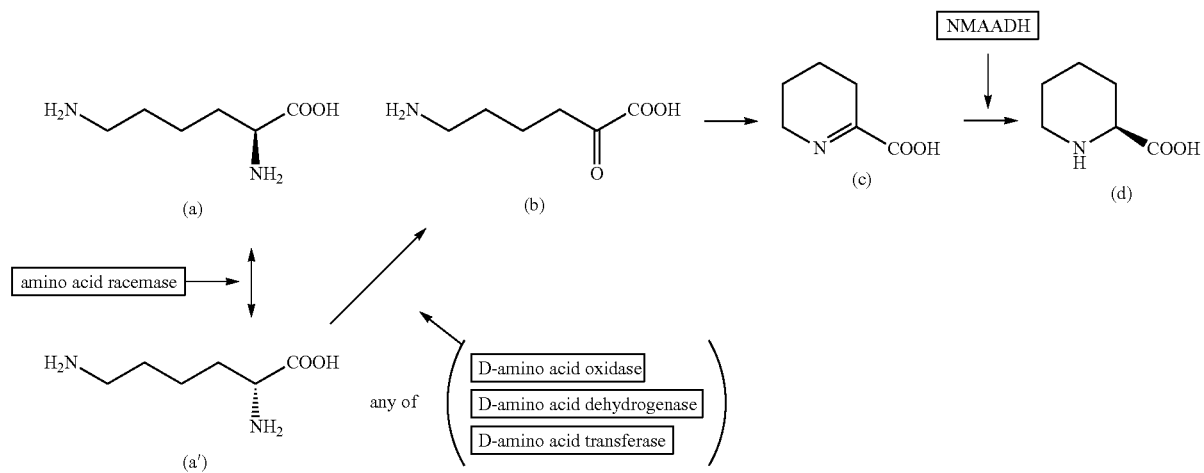

In Scheme (i-2), at least one enzyme selected from the group consisting of a D-amino acid oxidase, a D-amino acid dehydrogenase and a D-amino acid transferase, an amino acid racemase, and an N-methyl-L-amino acid dehydrogenase (NMAADH) are used.

First, the compound (a) (L-lysine) is converted to the compound (a') in the D-form (D-lysine) by an amino acid racemase, which is then converted to the compound (b) by an enzyme selected from the group consisting of a D-amino acid oxidase, a D-amino acid dehydrogenase and a D-amino acid transferase. The compound (b) is spontaneously converted to the compound (c). Then, the compound (c) is converted to the compound (d) (L-pipecolic acid) by an N-methyl-L-amino acid dehydrogenase (NMAADH).

The D-amino acid oxidase is not particularly limited as long as it is an enzyme which catalyze the substitution of the amino group at position 2 of D-lysine with an oxo group, but examples of the D-amino acid oxidase include a protein containing an amino acid sequence as described in Biochemistry, 2005, 70, pp. 40, or proteins each having an amino acid sequence with an identity of not less than 80%, preferably not less than 90%, and more preferably not less than 95% to the amino acid sequence of the above protein and having the activity thereof.

The D-amino acid dehydrogenase is not particularly limited as long as it is an enzyme which catalyze the substitution of the amino group at position 2 of D-lysine with an oxo group, but examples of the D-amino acid dehydrogenase include DauA described in Microbiology, 2010, 156 (Pt 1), pp. 60 and Proc. Natl. Acad. Sci. U.S.A., 2009, 106, pp. 906, or proteins each having an amino acid sequence with an identity of not less than 80%, preferably not less than 90/a, and more preferably not less than 95% to the amino acid sequence of DauA and maintaining the activity thereof.

The D-amino acid transferase (D-amino acid aminotransferase) is not particularly limited as long as it is an enzyme which catalyze the substitution of the amino group at position 2 of D-lysine with an oxo group, but examples of the D-amino acid transferase include D-AAT described in Protein Eng, 1998, 11. pp. 53, or proteins each having an amino acid sequence with an identity of not less than 80%, preferably not less than 90%, and more preferably not less than 95% to the amino acid sequence of D-AAT and maintaining the activity thereof.

The amino acid racemase (LysR) is not particularly limited as long as it is an enzyme which can catalyze the conversion of L-lysine to D-lysine, but examples of the amino acid racemase include LysR described in Appl. Microbiol. Biotechnol. 2015, 99, pp. 5045, or proteins each having an amino acid sequence with an identity of not less than 80%, preferably not less than 90%, and more preferably not less than 95% to the amino acid sequence of LysR and maintaining the activity thereof.

The N-methyl-L-amino acid dehydrogenase is not particularly limited as long as it is an enzyme which can catalyze the conversion of 3,4,5,6-tetrahydropyridine-2-carboxylic acid to L-pipecolic acid, but examples of the N-methyl-L-amino acid dehydrogenase include DpkA described in J. Biol. Chem. 2005, 280(49), pp. 40875, or proteins each having an amino acid sequence with an identity of not less than 80%, preferably not less than 90%, and more preferably not less than 95% to the amino acid sequence of DpkA and maintaining the activity thereof.

In the reactions indicated by Schemes (i-1) and (i-2), each step of the enzyme reaction may be separately performed, but it is preferred to sequentially perform the enzyme reaction steps in the same reaction system.

In cases where the above method is carried out continuously in the same reaction system, the method is preferably carried out in an aqueous medium containing L-lysine and cells transformed with a group of genes encoding the respective enzymes, products prepared from the transformants, and/or culture liquids obtained by culturing the transformants, or alternatively in a mixture of the aqueous medium and an organic solvent.

Because N-methyl-L-amino acid dehydrogenase (NMAADH) requires NAD(P)H as a coenzyme, it is preferred to allow a system for the regeneration of NAD(P)H from NAD(P)$^+$, which is generated in the reaction of NMAAH, to coexist in the same reaction system.

Exemplary methods for regeneration of NAD(P)H include 1) a method in which the ability of a host microorganism itself to reduce NAD(P), is utilized; 2) a method in which a microorganism having the ability to generate NAD(P)H from NAD(P)$^+$ or a product prepared therefrom, or an enzyme available for the regeneration of NAD(P)H (regeneration enzyme), such as glucose dehydrogenase, formate dehydrogenase, alcohol dehydrogenase, an amino acid dehydrogenase, or an organic acid dehydrogenase (such as malate dehydrogenase), is added to the reaction system; 3) a method in which genes for the above regeneration enzymes available for the regeneration of NAD(P)H are introduced together with the DNA according to the present invention into a host: and the like.

Among them, in the above-described regeneration method (1), compounds such as glucose, ethanol, formic acid, and the like are preferably added to the reaction system. Thus, these compounds are metabolized by a host, and NAD(P)H generated in the metabolic processes can be used in the reaction.

In the above-described regeneration method (2), as the regeneration enzymes, microorganisms containing those regeneration enzymes, or products prepared from microbial bodies of those microorganisms, such as those prepared by acetone treatment, freeze-drying, and physical or enzymatic disruption, may be used. Moreover, fractions containing the enzymes separated as crudely or finely purified materials from the products prepared from the microbial bodies, those immobilized on a carrier such as polyacrylamide gel or carrageenan gel, and the like may be used. Furthermore, commercially available products of the enzymes may be used.

In the above-described regeneration methods (2) and (3), a compound as a substrate for any of the regeneration enzymes is preferably added to allow the regeneration enzyme to exert its ability to reduce the coenzyme. For example, glucose, formic acid, and an alcohol such as ethanol or isopropanol are preferably added when a glucose dehydrogenase, a formic acid dehydrogenase, and an alcohol dehydrogenase are used, respectively.

As the cells containing the enzymes which catalyze the respective reaction steps, microorganisms inherently having these enzymes may be used, but it is preferred to use cells transformed with DNAs encoding the respective enzymes. In Scheme (i-1), it is preferred to use cells transformed with different DNAs encoding at least one enzyme selected from the group consisting of an L-amino acid oxidase, an L-amino acid dehydrogenase and an L-amino acid transferase, and an N-methyl-L-amino acid dehydrogenase (NMAADH). Moreover, in Scheme (i-2), it is preferred to use cells transformed with different DNAs encoding at least one enzyme selected from the group consisting of a D-amino acid oxidase, a D-amino acid dehydrogenase and a D-amino acid transferase, an amino acid racemase, and an N-methyl-L-amino acid dehydrogenase (NMAADH).

Moreover, each of these DNAs may be integrated into a chromosome, or these DNAs may be introduced into a single vector for use in transformation of a host, or each of these DNAs may be separately introduced into a vector for use in subsequent transformation of a host.

The transformation method for a host cell, such as a microorganism, the type of the host, and the like are the same as those as described above for the L-pipecolic acid hydroxylase.

The second method of producing L-pipecolic acid from L-lysine in the present invention is a production method as described below, the production method characterized by:

(ii) allowing L-lysine to react with one or more enzymes selected from the group consisting of an L-lysine 6-oxidase, an L-lysine 6-dehydrogenase and an L-lysine 6-aminotransferase, for the production of 2,3,4,5-tetrahydropyridine-2-carboxylic acid; and subsequently allowing a pyrroline-5-carboxylate reductase to act on the 2,3,4,5-tetrahydropyridine-2-carboxylic acid for the production of L-pipecolic acid.

The method will be described below by illustrating a scheme.

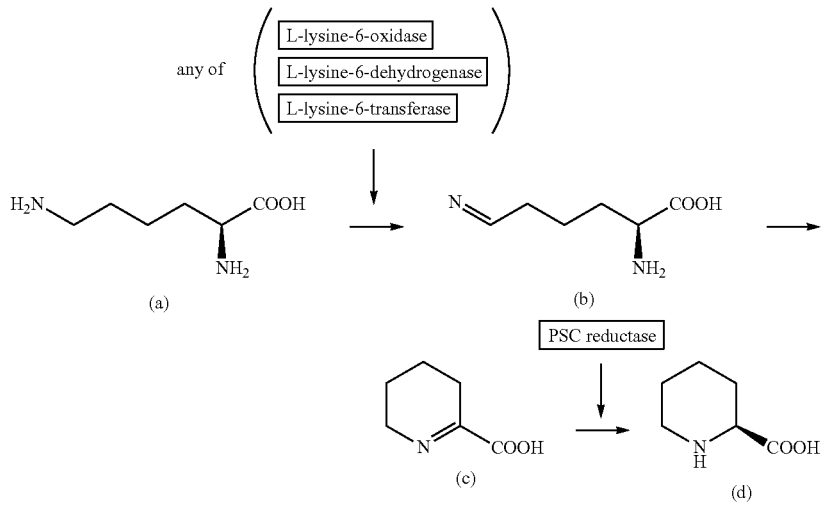

First, the compound (a)(L-lysine) is converted to the compound (b') by at least one enzyme selected from the group consisting of an L-lysine 6-oxidase, an L-lysine 6-dehydrogenase and an L-lysine 6-transferase. The compound (b') is spontaneously converted to the compound (c') (2,3,4,5-tetrahydropyridine-2-carboxylic acid). Then, the compound (c') is converted to the compound (d)(L-pipecolic acid) by a pyrroline-5-carboxylate (P5c) reductase.

The L-lysine 6-oxidase is not particularly limited as long as it is an enzyme which can catalyze the substitution of the amino group at position 6 of L-lysine with an oxo group, but examples of the L-lysine 6-oxidase include LodA described in Biochim. Biophys. Acta., 2006, 1764, pp. 1577, or proteins each having an amino acid sequence with an identity of not less than 80%, preferably not less than 90/a, is and more preferably not less than 95% to the amino acid sequence of LodA and maintaining the activity thereof.

The L-lysine 6-dehydrogenase is not particularly limited as long as it is an enzyme which can catalyze the substitution of the amino group at position 6 of L-lysine with an oxo group, but examples of the L-lysine 6-dehydrogenase include a protein containing an amino acid sequence as described in J. Biochem., 105, pp. 1002-1008 (1989), or proteins each having an amino acid sequence with an identity of not less than 80%, preferably not less than 90%, and more preferably not less than 95% to the amino acid sequence of the above protein and having the activity thereof.

The L-lysine 6-transferase (lysine-6-aminotransferase) is not particularly limited as long as it is an enzyme which can catalyze the substitution of the amino group at position 6 of hydroxy-L-lysine with an oxo group, but examples of the L-lysine 6-transferase include a protein containing an amino acid sequence as described in WO2001/048216, or proteins each having an amino acid sequence with an identity of not less than 80%, preferably not less than 90%, and more preferably not less than 95% to the amino acid sequence of the above protein and having the activity thereof.

The pyrroline-5-carboxylate (P5C) reductase is not particularly limited as long as it is an enzyme which can catalyze the conversion of 2,3,4,5-tetrahydropyridine-2-carboxylic acid to L-pipecolic acid, but examples of the pyrroline-5-carboxylate (P5C) reductase include a protein containing an amino acid sequence as described in WO2001/048216, or proteins each having an amino acid sequence with an identity of not less than 80%, preferably not less than 90%, and more preferably not less than 95% to the amino acid sequence of the above protein and having the activity thereof.

In the reaction of the production method for pipecolic acid (ii), each step of the enzyme reaction may be separately performed, but it is preferred to sequentially perform the enzyme reaction steps in the same reaction system. In particular, it is preferred to perform the reaction by allowing cells containing the enzymes, which catalyze the respective reaction steps, to react with L-lysine. As the cells containing the enzymes which catalyze the respective reaction steps, cells inherently having these enzymes may be used, but it is preferred to use cells transformed with DNAs encoding the respective enzymes. Specifically, it is preferred to use cells transformed with different DNAs encoding at least one enzyme selected from the group consisting of an L-lysine 6-oxidase, an L-lysine 6-dehydrogenase and an L-lysine 6-transferase, and a pyrroline-5-carboxylate (P5C) reductase.

The transformation method for a host cell, such as a microorganism, the type of the host, and the like are the same as those as described above for the L-pipecolic acid hydroxylase.

In cases where the second method (ii) is carried out continuously in the same reaction system, the method is preferably carried out in an aqueous medium containing L-lysine and cells transformed with a group of genes encoding the respective enzymes, products prepared from the transformants, and/or culture liquids obtained by culturing the transformants, or alternatively in a mixture of the aqueous medium and an organic solvent.

The third method of producing L-pipecolic acid from L-lysine in the present invention is a production method as described below, the production method characterized by:

(iii) allowing a lysine cyclodeaminase to act on L-lysine for the production of L-pipecolic acid.

The lysine cyclodeaminase is not particularly limited as long as it is an enzyme which can catalyze the conversion of L-lysine to L-pipecolic acid, but examples of the lysine cyclodeaminase include a protein containing an amino acid sequence as described in Biochimie 2007, 89, pp. 591, or proteins each having an amino acid sequence with an identity of not less than 80%, preferably not less than 90%, and more preferably not less than 95% to the amino acid sequence of the above protein and having the activity thereof.

It is preferred to perform the reaction by the lysine cyclodeaminase by allowing cells containing a lysine cyclodeaminase to react with L-lysine. As the microorganism containing a lysine cyclodeaminase, cells inherently having the enzymes may be used, but it is preferred to use a cell transformed with a DNA encoding a lysine cyclodeaminase.

The transformation method for a host cell, such as a microorganism, the type of the host, and the like are the same as those as described above for the L-pipecolic acid hydroxylase.

In cases where the conversion of L-lysine to L-pipecolic acid by a lysine cyclodeaminase is performed, the conversion is preferably performed in an aqueous medium containing L-lysine and cells transformed with a DNA encoding a lysine cyclodeaminase, a product prepared from the transformant, and/or a culture liquid obtained by culturing the transformant, or alternatively in a mixture of the aqueous medium and an organic solvent.

In the present invention, the L-pipecolic acid hydroxylase, the microorganism or cell having the ability to produce the enzyme, the processed product of the microorganism or cell, or the culture liquid comprising the enzyme and obtained by culturing the microorganism or cell can be contaminated with L-proline. In that case, the content of L-proline is not more than 10% (w/w), preferably not more than 1% (w/w), and particularly preferably not more than 0.1% (w/w).

Moreover, the microorganism or cell having the ability to produce an L-pipecolic acid hydroxylase may be a microorganism or cell having the ability to produce L-proline from an ingredient as a base material in the culture liquid or the reaction system.

Moreover, a solvent may be used when a hydroxy-L-pipecolic acid is produced. The solvent is not particularly limited, but the production of a hydroxy-L-pipecolic acid is preferably carried out in an aqueous solvent, or in a mixture of an aqueous solvent and an organic solvent.

Examples of the aqueous medium include water or buffers. Examples of the buffer include phosphate buffer, acetate buffer, borate buffer, Tris-HCl buffer, and the like.

Moreover, as an organic solvent to be used in the mixture, an organic solvent such as methanol, ethanol, 1-propanol, 2-propanol, 1-butanol, tert-butanol, acetone, or dimethyl sulfoxide, in which the solubility of the reaction substrate is high, may be used, while an organic solvent such as ethyl acetate, butyl acetate, toluene, chloroform, or n-hexane, which is effective in the removal of reaction by-products, and the like, may also be used.

The volume of the solvent is not particularly limited, but it is a volume normally in the range of 0.01% (w/v) to 90/o (w/v), and preferably in the range of 0.1% (w/v) to 10% (w/v), to the L-pipecolic acid as the substrate.

The concentration of the L-pipecolic acid as the substrate in the reaction system is normally in the range of 0.01% (w/v) to 90% (w/v), and preferably in the range of 0.1% (w/v) to 30% (w/v). The L-pipecolic acid may be added in one portion to the reaction system when the reaction is initiated, but is desirably added to the reaction system in a continuous or intermittent fashion in view of the inhibitory effect on the substrate of the enzyme, if any, to be reduced, the increase in the concentration of the accumulated product, and the like.

The amount of 2-oxoglutaric acid to be added is an amount equimolar to or greater than that of the L-pipecolic acid as the substrate, and is preferably an amount ranging from 1 to 1.2 times the number of moles of the L-pipecolic acid as the substrate. The 2-oxoglutaric acid may be added in one portion to the reaction system when the reaction is initiated, but is desirably added to the reaction system in a continuous or intermittent fashion in view of the inhibitory effect on the substrate of the enzyme, if any, to be reduced, the increase in the concentration of the accumulated product, and the like.

Moreover, an inexpensive compound that can be metabolized by the host, such as glucose, may be added instead of 2-oxoglutaric acid to the reaction system, which compound is metabolized by the host and the resulting 2-oxoglutaric acid produced during this process may be allowed to exist in the reaction system.

The concentration of ferrous ion in the reaction system normally from 0.0001 to 0.5 mol, preferably from 0.001 to 0.1 mol, per mol of L-pipecolic acid.

The ferrous ion may be added in one portion, normally in the form of ferrous sulfate, ferrous chloride, ferrous citrate, and the like, to the reaction system when the reaction is initiated. When the added ferrous ions are oxidized to ferric ions or precipitated during the reaction and the level of ferrous ions is thus decreased, it is also effective to add an additional amount of ferrous ion until a desired concentration is achieved.

Moreover, in cases where ferrous ions have already been contained at a desired concentration in the L-pipecolic acid hydroxylase of the present invention, the microorganism or cell having the ability to produce the enzyme, the processed product of the microorganism or cell, and/or the culture liquid comprising the enzyme and obtained by culturing the microorganism or cell, the addition of ferrous ion is not necessarily required.

The reaction is carried out at a reaction temperature of normally 4° C. to 60° C. preferably 15° C. to 45° C., and particularly preferably 20° C. to 40° C., and at a pH of normally 3 to 11, preferably 5 to 8. The reaction time is normally about 1 hour to about 150 hours.

The L-pipecolic acid hydroxylase, the microorganism or cell having the ability to produce the enzyme, the processed product of the microorganism or cell, and/or the culture liquid comprising the enzyme and obtained by culturing the microorganism or cell are/is in such an amount that, for example, the concentration of the microorganism or cell in the reaction system is normally in the range of 0.1% (w/v) to 50% (w/v), preferably 1% (w/v) to 20% (w/v), in terms of wet cell weight if the microorganism or cell is used. Moreover, if the processed product or the culture liquid is used, the processed product or the culture liquid is used in an amount based on the calculated specific activity of the enzyme, which corresponds to the concentration of the microorganism or cell in the reaction system as described above.

Produced hydroxy-L-pipecolic acids can be purified as follows: after the completion of the reaction, microbial bodies, proteins and the like in the reaction system are separated by centrifugation, membrane filtration, and the like; a hydroxy-L-pipecolic acid is subsequently purified by an appropriate combination of extraction with an organic solvent, such as 1-butanol, tert-butanol, or like; distillation; column chromatography using an ion exchange resin, silica gel and the like; isoelectric precipitation; crystallization with a salt, such as monohydrochloride salts, dihydrochloride salts and calcium salts; and the like.

EXAMPLES

Now, the present invention will be described in more detail by way of examples but is not limited thereto.

<Example 1> Cloning of L-Pipecolic Acid Hydroxylase Genes

A gene encoding the amino acid hydroxylase McPH (GenBank Accession No. WP_030487089; SEQ ID NO: 2), which is annotated as an aspartyl beta-hydroxylase derived from a *Micromonospora chokoriensis* strain, was artificially synthesized as a gene sequence codon-optimized for expression in *E. coli* (mcph_OE; SEQ ID NO: 1). The gene was inserted into pJExpress411 (DNA2.0) to construct the plasmid pJ411McPH.

Similarly, four genes for enzymes exhibiting the activity to catalyze the hydroxylation of L-pipecolic acid at position 5 were cloned.

Thhe codon-optimized gene sequences sruph_OE (SEQ ID NO: 3), caph_OE (SEQ ID NO: 5), and xdph_OE (SEQ ID NO: 7) for expression in *E. coli*, which respectively encode the L-pipecolic acid ci-5-hydroxylase SruPH (GenBank Accession No. EFV12517; SEQ ID NO: 4) derived from the *Segniliparus rugosus* strain ATCC BAA-974, the L-proline cis-4-hydroxylase CaPH (GenBank Accession No. WP_012787640; SEQ ID NO: 6) derived from the *Catenulispora acidiphila* strain NBRC102108, and the L-proline cis-4-hydroxylase XdPH (GenBank Accession No. CDG16639; SEQ ID NO: 8) derived from the *Xenorhabdus doucetiae* strain FRM16, were artificially synthesized.

The respective genes were inserted into pJexpress411 (manufactured by DNA2.0) and obtained as plasmids, which were named pJ411SruPH, pJ411CaPH, and pJ411XdPH.

The codon-optimized gene sequence smph_OE (SEQ ID NO: 9) for expression in *E. coli*, which encodes the L-proline cis-4-hydroxylaseSmPH (GenBank Accession No. CAC47686; SEQ ID NO: 10) derived from the *Sinorhizobium meliloti* strain 1021, was artificially synthesized and inserted into pJexpress401 to produce the plasmid pJ401SmPH. For the smph_OE, the primers smph_f (SEQ ID NO: 21) and smph_r (SEQ ID NO: 22) were synthesized and used for PCR reaction using the plasmid DNA as a template according to a conventional method to obtain a DNA fragment with a length of about 1.0 kbp. The obtained DNA fragment was digested with the restriction enzymes Nde I and Hind III and then ligated according to a conventional method into pET24a (Novagen) digested with Nde I and Hind III to obtain pET24SmPH.

A gene encoding the amino acid hydroxylase KjPH (GenBank Accession No. WP_046758372; SEQ ID NO: 18), which is annotated as a hypothetical protein derived from a *Kordia jejudonensis* strain, was artificially synthesized as a gene sequence codon-optimized for expression in *E. coli* (kjph_OE; SEQ ID NO: 17). The gene was inserted into pJExpress411 (DNA2.0) to construct the plasmid pJ411KjPH.

Moreover, three genes for enzymes exhibiting the activity to catalyze the hydroxylation of L-pipecolic acid at position 4 were cloned.

The codon-optimized gene sequences cgph_OE (SEQ ID NO: 11), peph_OE (SEQ ID NO: 13), and gzph_OE (SEQ ID NO: 15) for expression in *E. coli*, which respectively encode the L-pipecolic acid trans-4-hydroxylase CgPH (GenBank Accession No. ELA34460; SEQ ID NO: 12) derived from *Colletotrichum gloeosporioides* strain Nara qc5, the L-pipecolic acid trans-4-hydroxylase PcPH (GenBank Accession No. XP_002558179; SEQ ID NO: 14) derived from the *Penicillium chrysogemum* strain Wisconsin 54-1255, and the L-pipecolic acid trans-4-hydroxylase GzPH (GenBank Accession No. XP_383389; SEQ ID NO: 16) derived from the *Gibberella zeae* strain PH-1, were artificially synthesized.

Details about the above-described cloned L-pipecolic acid hydroxylases are shown in Table 1.

TABLE 1

| SEQ ID NO. | ID | Microorganism of origin | Accession No. |
|---|---|---|---|
| 2 | McPH | *Micromonospora chokoriensis* | WP_030487089 |
| 4 | SruPH | *Segniliparus rugosus* ATCC BAA-974 | EFV12517 |
| 6 | CaPH | *Catenulispora acidiphila* NBRC102108 | WP_012787640 |
| 8 | XdPH | *Xenorhabdus doucetiae* FRM16 | CDG16639 |
| 10 | SmPH | *Sinorhizobium meliloti* 1021 | CAC47686 |
| 12 | CgPH | *Colletotrichum gloeosporioides* Nara gc5 | ELA34460 |
| 14 | PcPH | *Penicillium chrysogenum* Wisconsin 54-1255 | XP_002558179 |
| 16 | GzPH | *Gibberella zeae* PH-1 | XP_383389 |
| 18 | KjPH | *Kordia jejudonensis* | WP_046758372 |

<Example 2> Obtainment of L-Pipecolic Acid Hydroxylase Gene-Expressing Bacteria

Each of the plasmids obtained in Example 1 was used to transform *E. coli* (*Escherichia coli*) BL21 (DE3)(manufactured by Invitrogen) according to a conventional method and thus to obtain the recombinant *E. coli* BL21 (DE3ypJ411McPH, BL21 (DE3)/pJ411SruPH, BL21 (DE3pJ411CaPH, BL21 (DE3ypJ411XdPH, BL21 (DE3)/pET24SmPH, BL21 (DE3ypJ411CgPH, BL21 (DE3YpJ411PcPH, BL21 (DE3)/pJ411GzPH, and BL21 (DE3)/pJ411KjPH.

To obtain bacteria expressing each of the introduced genes, each recombinant *E. coli* strain was cultured using liquid LB medium containing kanamycin and a lac promoter-inducible substance for about five hours at 30° C. and then for about 30 hours at 18° C., followed by harvest of the bacteria.

Each of the obtained recombinant *E. coli* strains in a volume of 0.6 mL was recovered by centrifugation and was suspended in 0.5 mL of 50 mmol/L MES (2-morpholinoethanesulfonic acid) buffer at pH 6. The container containing the suspension was placed in ice-water bath to perform sonication and then spun at 12,000 rpm. The obtained supernatant was used as an enzyme solution in Example 3.

<Example 3> Determination of the Catalytic Efficiency (Kcat/Km) of the L-Pipecolic Acid Hydroxylase with L-Pipecolic Acid and L-Proline Several L-pipecolic acid hydroxylases were examined for the catalytic efficiency with L-pipecolic acid and L-proline.

To a plastic tube, L-pipecolic acid at a final concentration ranging from 0.3 mmol/L to 50 mmol/L, 2-oxoglutaric acid at 20 mmol/L, L-ascorbic acid at 1 mmol/L, ferrous sulfate (11) at 0.5 mmol/L, and each enzyme solution obtained in Example 2 at a protein concentration of about 2 mg/mL were added; then, the obtained reaction solution in a volume of 0.2 mL was shaken at 30° C. for 25 minutes. Subsequently, 0.05 mL of 1 mol/L hydrochloric acid was added to stop the reaction.

The reaction using L-proline as a substrate was carried out under the same conditions as in the above reaction using L-pipecolic acid.

Then, each reaction solution was treated using l-fluoro-2,4-dinitrophenyl-S-L-alaninamide (FDAA) (manufactured by Tokyo Chemical Industry Co., Ltd.) according to a method as described below, to obtain a FDAA-derivative of a hydroxy-L-pipecolic acid or hydroxy-L-proline included in each reaction solution.

To the reaction solution after stopping the reaction, 0.05 mL of 1 mol/L sodium hydroxide was added for neutralization. After centrifuging the solution at 12,000 rpm, 15 µL of 0.5 mol/L borate buffer (pH 9) was added to 15 µL of the obtained supernatant, followed by further addition of 30 µL of 20 mmol/L FDAA solution in acetone and incubation at 40° C. for one hour. Subsequently, 10 µL of 1 mol/L hydrochloric acid was added to stop the derivatization reaction. The resulting solution was diluted by adding 80 µL of methanol, and then centrifuged at 12,000 rpm. The obtained supernatant was used as a FDAA derivative solution.

The amount of produced hydroxy-L-pipecolic acid or hydroxy-L-proline was analyzed with UPLC-MS (manufactured by Waters Co.). The analytical conditions are shown in Tables 2 to 4.

The (5S)-hydroxy-L-pipecolic acid-producing activity or (4R)-hydroxy-L-pipecolic acid-producing activity (U/mg) indicated by each enzyme solution was defined by units (U) per milligram of each hydroxylase (mg). One unit herein represents the ability to produce 1 µmol of a hydroxy-L-pipecolic acid in the period of 1 minute.

TABLE 2

| LC settings | |
|---|---|
| Used instruments | ACQUITY SQD UPLC/MS (manufactured by Waters Co.) |
| Analytical column | ACQUITY UPLC BEH C18 Column(manufactured by Waters Co.) |
| Column temp. | 30° C. |
| Eluent | A  0.1% formic acid/water solution |
|  | B  0.1% formic acid/acetonitrile solution |

TABLE 3

| Elution conditions | | | |
|---|---|---|---|
| Time (min) | A (%) | B (%) | Flow rate (ml/min) |
| 0 | 80 | 20 | 0.2 |
| 12 | 45 | 55 | |
| 12.5 | 0 | 100 | |
| 14.5 | 0 | 100 | |
| 14.6 | 80 | 20 | |
| 18 | 80 | 20 | |

TABLE 4

MS conditions

| Used instruments | SQ Detector (manufactured by Waters Co.) |
|---|---|
| Settings | Ion mode ESI Positive |
| | Capillary Voltage (kV) 3.0 |
| | Cone Voltage (V) 50 |
| | Extractor Voltage (V) 3 |
| | RF Lens Voltage (V) 0.1 |
| | Source Temp. (° C.) 130 |
| | Desolvation Temp. (° C.) 350 |
| | Desolvation Gas Flow (L/hr) 600 |
| | Cone Gas Flow (L/hr) 50 |

The amount of each hydroxylase was quantified as described below.

An aliquot containing 5 μg of total protein was taken from each enzyme solution obtained in Example 2, loaded on each lane, and then electrophoresed on polyacrylamide gel. The obtained electrophoretogram was analyzed using the image analysis software Image Lab3.0 (manufactured by Bio-Rad Laboratories, Inc.) to determine the content of each hydroxylase. A carbonic anhydrase (manufactured by Sigma-Aldrich Co. LLC) was used as a quantification reference. The content of a hydroxylase of interest was calculated from the signal intensity of the enzyme of interest, based on the signal intensities of bands corresponding to 200 ng, 400 ng and 600 ng of the quantification reference provided for the electrophoresis.

The catalytic efficiency of each enzyme was calculated based on the Michaelis-Menten kinetic equation.

First, the reciprocals of the respective concentrations of L-pipecolic acid (mmol/L) and the reciprocals of the hydroxy-L-pipecolic acid-producing activities per milligram of each hydroxylase (U/mg) at the respective concentrations of L-pipecolic acid were plotted on the x-axis and the y-axis, respectively, where there are four to six data points in the range of 0.3 mmol/L to 50 mmol/L of L-pipecolic acid (FIG. 1). It is known that, in FIG. 1, the reciprocal of each intercept with the x-axis, multiplied with −1, represents a km value (mmol/L) and the reciprocal of each intercept with the y-axis represents a Vmax value (U/mg), the maximum rate of reaction.

The catalytic ability per molecule of the enzyme (kcat) can be calculated from the Vmax and the molecular weight of the enzyme. Table 5 indicates the result of the calculation of catalytic efficiency (kcat/km), which is an index representing the catalytic ability of an enzyme, based on the obtained kcat and km values.

When L-proline was used as a substrate, a much amount of hydroxy-L-proline was detected from the reaction solution using the hydroxylase CaPH. Moreover, a small amount of hydroxy-L-proline was detected from the reaction solutions of the hydroxylases SruPH, XdPH, SmPH, and KjPH. On the other hand, no hydroxy-L-proline was detected from the reaction solution of the hydroxylase McPH. Based on this result, it is understood that McPH is a novel enzyme having the 5-hydroxypipecolic acid-producing activity and characterized by a very low reactivity with proline. This property is not easily deduced from known facts.

Also, no hydroxy-L-proline was detected from the reaction solutions of the hydroxylases CgPH, PcPH, and GzPH. Based on this result, it was found that these hydroxylases were novel enzymes having the 4-hydroxypipecolic acid-producing activity and characterized by a very low reactivity with proline. This property is not easily deduced from known facts.

TABLE 5

| Name | Molecular weight | Substrate L-pipecolic acid | | | | Substrate L-proline | | | | A value of the catalytic reaction efficiency for L-proline relative to the catalytic reaction efficiency for L-pipecolic acid |
|---|---|---|---|---|---|---|---|---|---|---|
| | | Km (mM) | Vmax (U/mg-protein) | kcat | kcat/Km | Km (mM) | Vmax (U/mg-protein) | kcat | kcat/Km | |
| (S-hydroxy-L-pipecolic acid-producing enzyme) | | | | | | | | | | |
| MoPH | 31872 | 0.24 | 0.06 | 0.03 | 0.13 | (No activity) | | | | 0 |
| SruPH | 33774 | 1.09 | 0.06 | 0.03 | 0.02 | 0.40 | 0.13 | 0.07 | 0.18 | 754% |
| CaPH | 32503 | (No activity) | | | | 8.87 | 0.02 | 0.01 | 0.00 | — |
| XdPH | 33475 | 0.30 | 1.14 | 0.64 | 2.16 | 0.31 | 1.44 | 0.80 | 2.56 | 119% |
| SmPH | 32019 | 0.31 | 0.03 | 0.02 | 0.05 | 0.58 | 0.06 | 0.03 | 0.06 | 114% |
| KlPH | 32277 | 0.49 | 0.30 | 0.16 | 0.33 | 0.45 | 0.34 | 0.18 | 0.36 | 115% |
| (4-hytoxy-L-pipecolic acid producing enzyme) | | | | | | | | | | |
| CgPH | 37320 | 8.56 | 70.42 | 43.80 | 5.12 | (No activity) | | | | 0 |
| PcPH | 32130 | 3.67 | 16.16 | 8.85 | 2.36 | (No activity) | | | | 0 |
| GzpH | 37835 | 4.72 | 114.94 | 72.48 | 15.36 | (No activity) | | | | 0 |

<Example 4> Comparison of the Reactivity Among L-Pipecolic Acid 5-Hydroxylases

The L-pipecolic acid 5-hydroxylases were compared for the reactivity with L-proline and L-pipecolic acid.

To a plastic tube, L-pipecolic acid or L-proline at 10 mmol/L, 2-oxoglutaric acid at 20 mmol/L, L-ascorbic acid at 1 mmol/L, ferrous sulfate at 0.5 mmol/L. and each enzyme solution obtained in Example 2 at a total protein concentration of about 2 mg/mL were added; then, the obtained reaction solution in a volume of 0.2 mL was shaken at 30° C. for 30 minutes. The amounts of produced hydroxy-L-pipecolic acid and hydroxy-L-proline were determined by the same method based on the derivatization with FDAA as in Example 3. The detection of the products was based on the absorbance at a wavelength of 340 nm.

Figure 2:
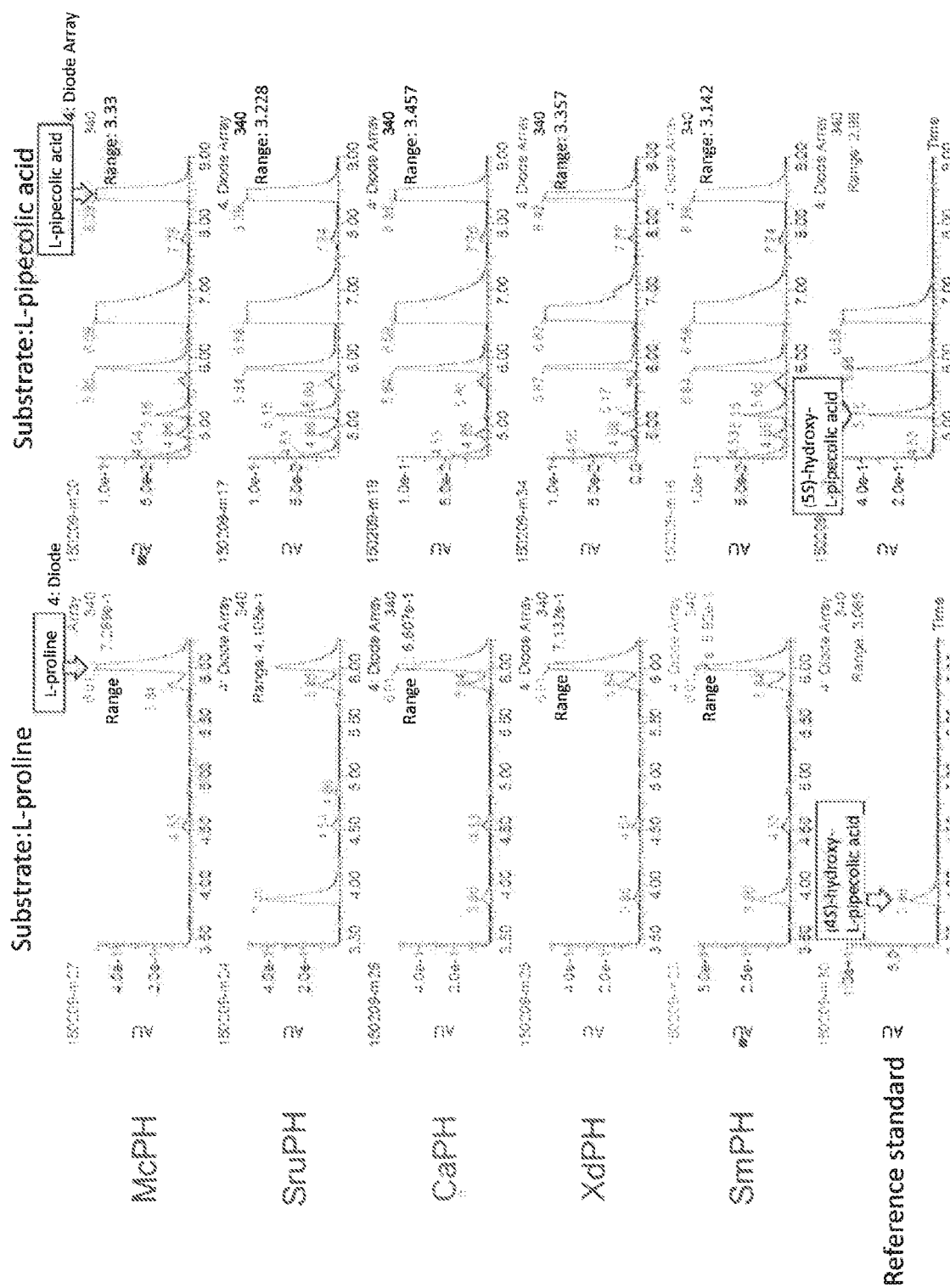
FIG. 2 indicates the reactivity with L-proline and L-pipecolic acid in L-pipecolic acid 5-hydroxylases compared in Example 4.

FIG. 2 shows chromatograms from the LC analysis of the reaction solutions derivatized with FDAA. The activity values were evaluated by the amount of a product per gram of total protein (U/g-protein). The hydroxy-L-proline-producing activity (relative activity) of each sample is presented in Table 6, where a ratio of 100% corresponds to the hydroxy-L-pipecolic acid-producing activity of the same reaction solution.

As indicated in FIG. 2 and Table 6, a much amount of hydroxy-L-proline was detected from the reaction solution of the hydroxylase CaPH. Moreover, a small amount of hydroxy-L-proline was detected from the reaction solutions of the hydroxylases SruPH, XdPH, and SmPH. No hydroxy-L-proline was detected from the reaction solution of the hydroxylase McPH.

Based on this result, it is understood that McPH is a novel enzyme having a high 5-hydroxypipecolic acid-producing activity and characterized by a very low reactivity with proline. This property is not easily deduced from known facts.

Moreover, the hydroxylases SruPH, XdPH, and SmPH were found to be enzymes having a high 5-hydroxypipecolic acid-producing activity and characterized by a low reactivity with proline. This property is not easily deduced from known facts.

TABLE 6

Relative activity
(A value of the hydroxy-L-proline-producing activity, where a value of 100 corresponds to the hydroxy-L-pipecolic acid-producing activity)

| Enzyme | Substrate: L-pipecolic acid | Substrate: L-proline |
| --- | --- | --- |
| McPH | 100 | 0 |
| SruPH | 100 | 59 |
| CaPH | 100 | 583 |
| XdPH | 100 | 37 |
| SmPH | 100 | 46 |

<Example 5> Production of Hydroxy-L-Pipecolic Acids

Eight recombinant E. coli strains obtained in Example 2, that is, BL21 (DE3)/pJ411McPH, BL21 (DE3)/pJ411SruPH, BL21 (DE3)/pJ411CaPH, BL21 (DE3)/pJ411XdPH, BL21 (DE3)/pET24SmPH. BL21 (DE3)/pJ411CgPH, BL21 (DE3)/pJ411PcPH and BL21 (DE3)/pJ411GzPH were inoculated to liquid M9 medium for starter culture (33.9 g/L Na$_2$HPO$_4$, 15 g/L KH$_2$PO$_4$, 2.5 g/L sodium chloride, 5 g/L ammonium chloride, 10 g/L casamino acid, 0.1 mmol/L calcium chloride, 0.1 mmol/L ferrous sulfate, 4 g/L glucose, 0.001 mmol/L magnesium chloride) containing kanamycin sulfate (25 μg/mL), and cultured at 30° C. for 24 hours under shaking conditions at 200 rpm.

Forty μL of the culture liquid was added to liquid M9 medium for main culture (50.9 g/L Na$_2$HPO$_4$, 22.5 g/L KH$_2$PO$_4$, 3.8 g/L sodium chloride, 7.5 g/L ammonium chloride, 10 g/L casamino acid, 0.1 mmol/L calcium chloride, 0.1 mmol/L ferrous sulfate, 20 mmol/L L-pipecolic acid, 12.5 g/L glycerol) containing kanamycin sulfate (25 μg/mL) and Overnight Express Autoinduction Systems (Merck KGaA), and then cultured at 30° C. for 120 hours under shaking conditions at 200 rpm.

Samples for analysis were prepared by collecting and centrifuging the culture 48, 64, and 120 hours after the start of culture, and then recovering the supernatants, and the prepared samples were subjected to LC and MS analyses.

The samples for analysis were treated using FDAA (manufactured by Tokyo Chemical Industry Co., Ltd.) according to a method as described below, to obtain a FDAA-derivative.

After centrifuging the sample solutions for analysis, 27 μL of 0.5 mol/L borate buffer (pH 9) was added to 3 μL of each supernatant, followed by further addition of 30 μL of 20 mmol/L FDAA solution in acetone and incubation at 40° C. for one hour. Subsequently, 10 μL of 1 mol/L hydrochloric acid was added to stop the reaction. The resulting solution was diluted by adding 80 L of methanol, and then centrifuged at 12,000 rpm. The obtained supernatant was used as a FDAA derivative solution.

The obtained FDAA derivative solution was analyzed for the amounts of a hydroxy-L-pipecolic acid and hydroxy-L-proline under LC/MS conditions indicated in Table 2. The obtained result is shown in FIG. 3 and FIG. 4.

Figure 3:
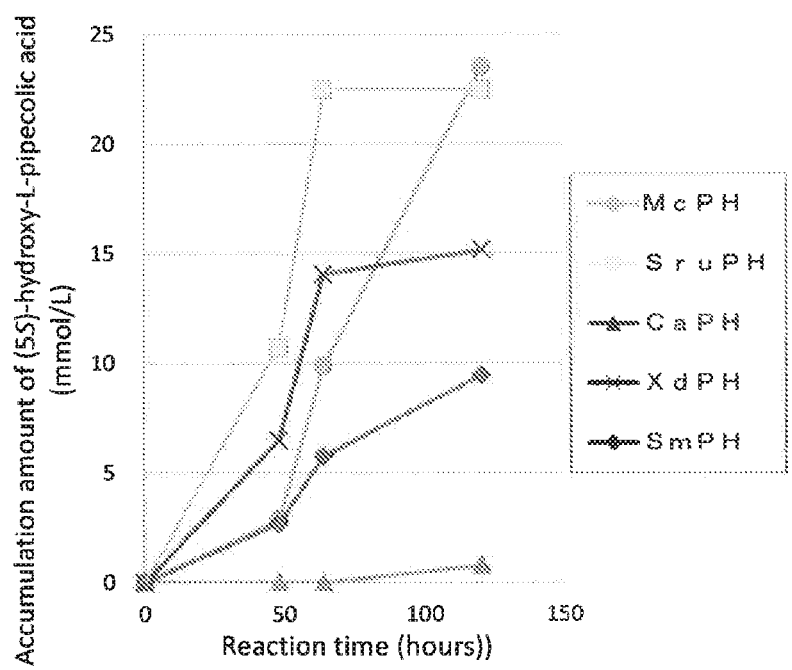
FIG. 3 shows the temporal change in amount of accumulated (5S)-hydroxy-L-pipecolic acid in Example 5.
Figure 4:
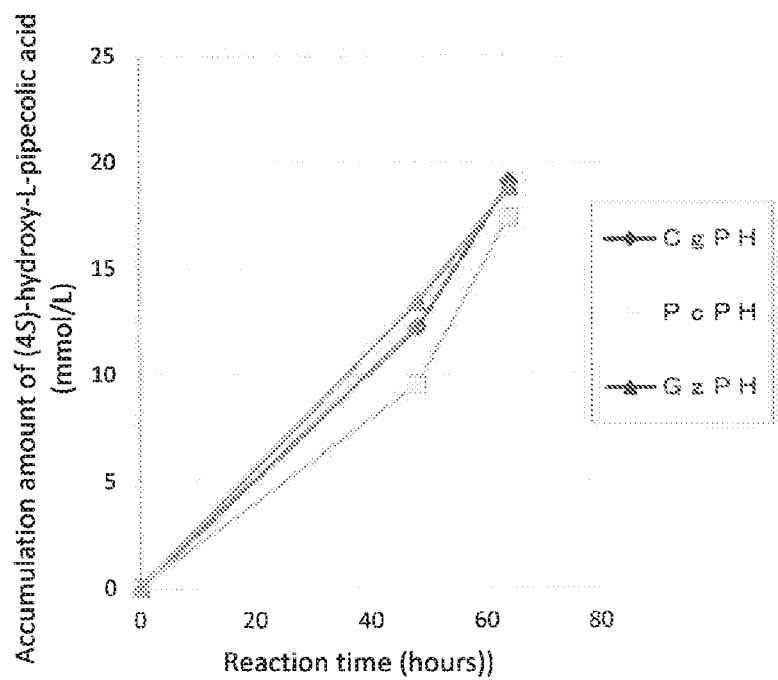
FIG. 4 shows the temporal change in amount of accumulated (4S)-hydroxy-L-pipecolic acid in Example 5.

FIG. 3 and Table 7 indicate the result on productivity obtained when (5S)-hydroxy-L-pipecolic acid-producing enzymes are used. FIG. 3 shows the temporal change in amount of accumulated (5S)-hydroxy-L-pipecolic acid. Table 7 shows the accumulation amount of each component determined for the samples of 120 hours post inoculation. It is indicated that almost the entire amount of the substrate was allowed to convert to (5S)-hydroxy-L-pipecolic acid by incubation with the hydroxylases SruPH and McPH for 120 hours.

TABLE 7

Accumulation amount of each component after 120 hours

| Name of enzyme | (5S)-Hydroxy-L-pipecolic acid (mmol/L) | L-pipecolic acid (mmol/L) | (4S)-hydroxy-L-proline (mmol/L) |
| --- | --- | --- | --- |
| McPH | 23.5 | 1.8 | 0 |
| SruPH | 22.5 | 0.1 | 1.8 |
| CaPH | 0.8 | 18.8 | 0 |
| XdPH | 15.2 | 10.6 | 0.3 |
| SmPH | 9.4 | 5.6 | 0.2 |

Accumulation of (4S)-hydroxy-L-proline was confirmed in the hydroxylases SruPH, XdPH, and SmPH, in which the reactivity with proline is identified in Example 3. No accumulation of (4S)-hydroxy-L-proline was confirmed in McPH. Also, no accumulation of (4S)-hydroxy-L-proline is confirmed in the hydroxylase CaPH; however, it is likely due to a small capacity of the hydroxylase CaPH as a hydroxylase because the accumulated amount of (5S)-hydroxy-L-pipecolic acid is also small.

Based on these results, it is understood that the hydroxylase McPH is a very practical hydroxylase having a high productivity of (5S)-hydroxy-L-pipecolic acid and characterized by no accumulation of by-products which are hardly removed during the purification steps, such as (4S)-hydroxy-L-proline.

FIG. 4 and Table 8 indicate the result on productivity obtained when (4S)-hydroxy-L-pipecolic acid-producing enzymes are used. FIG. 4 shows the temporal change in amount of accumulated (4S)-hydroxy-L-pipecolic acid. Table 8 shows the accumulation amount of each component determined for the samples of 64 hours post inoculation. It is indicated that a major amount of the substrate was allowed to convert to (4S)-hydroxy-L-pipecolic acid by incubation with the hydroxylases CgPH, PcPH, and GzPH for 64 hours. Moreover, no accumulation of (4R)-hydroxy-L-proline was confirmed.

Based on these results, it is understood that the hydroxylases CgPH, PcPH, and GzPH are very practical hydroxylases having a high productivity of (4S)-hydroxy-L-pipecolic acid and characterized by no accumulation of by-products which are hardly removed during the purification steps, such as (4R)-hydroxy-L-proline.

TABLE 8

Accumulation amount of each component after 64 hours

| Name of enzyme | (4S)-hydroxy-L-pipecolic acid (mmol/L) | L-pipecolic acid (mmol/L) | (4R)-hydroxy-L-proline (mmol/L) |
|---|---|---|---|
| CgPH | 19.1 | 0.2 | 0 |
| PcPH | 17.4 | 2.1 | 0 |
| GzPH | 18.8 | 0.2 | 0 |

<Example 6> Modification of the Gene for the Hydroxylase McPH Through Mutagenesis A plasmid encoding a mutant (McPHm1) was constructed using, as a template, the plasmid pJ411McPH obtained in Example 1 as well as using a set of the primer represented by SEQ ID NO: 23 (H4Q-f) and the primer represented by SEQ ID NO: 24 (H4Q-r) indicated in the Sequence Listing, where the QuikChange Multi Site-Directed Mutagenesis Kit (manufactured by Stratagene) was used to replace histidine with glutamine at amino acid position 4.

Plasmids were constructed in the same manner as described above, where a set of the primer represented by SEQ ID NO: 25 (F5Y-f) and the primer represented by SEQ ID NO: 26 (F5Y-r), a set of the primer represented by SEQ ID NO: 27 (C23A-f) and the primer represented by SEQ ID NO: 28 (C23A-r), a set of the primer represented by SEQ ID NO: 29 (C44A-f) and the primer represented by SEQ ID NO: 30 (C44A-r), a set of the primer represented by SEQ ID NO: 31 (L97R-f) and the primer represented by SEQ ID NO: 32 (L97R-r), a set of the primer represented by SEQ ID NO: 33 (V98A-f) and the primer represented by SEQ ID NO: 34 (V98A-r), a set of the primer represented by SEQ ID NO: 35 (D116G-f) and the primer represented by SEQ ID NO: 36 (D116G-r), a set of the primer represented by SEQ ID NO: 37 (C137A-f) and the primer represented by SEQ ID NO: 38 (C137A-r), and a set of the primer represented by SEQ ID NO: 39 (D282E-f) and the primer represented by SEQ ID NO: 40 (D282E-r) were designed and used to replace phenylalanine with tyrosine at position 5 (McPHm2), cysteine with alanine at position 23 (McPHm3), cysteine with alanine at position 44 (McPHm4), leucine with arginine at position 97 (McPHm5), valine with alanine at position 98 (McPHm6), aspartic acid with glycine at position 116 (McPHm7), cysteine with alanine at position 137 (McPHm8), and aspartic acid with glutamic acid at position 282 (McPHm9), respectively.

Each of the obtained plasmids was used to transform E. coli(Escherichia col) BL21 (DE3)(manufactured by Invitrogen) according to a conventional method and thus to obtain recombinant E. coli strains expressing the respective mutants. Enzyme solutions were prepared according to the method described in Example 2 from the obtained recombinant E. coli strains and evaluated for the activity to catalyze the hydroxylation of L-pipecolic acid at position 5 according to the method described in Example 4. The activity values were evaluated by the amount of a product per gram of total protein (U/g-protein). The activity value (relative activity) of each mutant is presented in Table 9, where a ratio of 100% corresponds to the 5-hydroxy-L-pipecolic acid-producing activity of the wild-type enzyme (McPH) without any mutation.

TABLE 9

| Mutant | Mutated position | Relative activity |
|---|---|---|
| (Wild type) | — | 100 |
| McPHm1 | H4Q | 82 |
| McPHm2 | F5Y | 132 |
| McPHm3 | C23A | 123 |
| McPHm4 | C44A | 0 |
| McPHm5 | L99R | 18 |
| McPHm6 | V100A | 2 |
| McPHm7 | D116G | 27 |
| McPHm8 | C137A | 42 |
| McPHm9 | D282E | 152 |

Furthermore, the combination effect of the respective mutations was examined in the mutations corresponding to McPHm2, McPHm3, and McPHm9, each of which was effective to improve the activity. A plasmid expressing a double mutant (McPHm10) with substitutions of phenylalanine to tyrosine at position 5 and cysteine to alanine at position 23, and a plasmid expressing a triple mutant, which is derived from the double mutant and further has a substitution of aspartic acid to glutamic acid at position 282, were constructed. Then, recombinant E. coli strains were produced according to the method described above, and the resulting enzyme solutions were used to evaluate the 5-hydroxy-L-pipecolic acid-producing activity. The result is presented in Table 10. The triple mutant McPHm11 (SEQ ID NO: 20; a gene encoding the same amino acid sequence is represented by SEQ ID NO: 19) exhibited an activity three or more times higher than that of the wild-type enzyme.

TABLE 10

| Mutant | Mutated position 1 | Mutated position 2 | Mutated position 3 | Relative activity |
|---|---|---|---|---|
| (Wild type) | — | — | — | 100 |
| McPHm10 | F5Y | C23A | — | 133 |
| McPHm11 | F5Y | C23A | D282E | 314 |

As for McPHm10 and McPHm11, the hydroxylation activity was determined in accordance with the method described in Example 4, where L-proline was used as a substrate. Thus, virtually no activity against proline was confirmed in both cases.

What is claimed is:

1. L-pipecolic acid hydroxylase, comprising a protein consisting of an amino acid sequence with an identity of not less than 90% to the amino acid sequence of SEQ ID NO: 2, the protein has one or more amino acid substitution with other amino acid selected from: substitution of phenylalanine at position 5, substitution of cysteine at position 23, and substitution of aspartic acid at position 282.

2. The L-pipecolic acid hydroxylase according to claim 1, wherein the protein has one or more amino acid substitution selected from: substitution of phenylalanine with tyrosine at position 5, substitution of cysteine with alanine at position 23, and substitution of aspartic acid with glutamic acid at position 282.

3. The L-pipecolic acid hydroxylase according to claim 1, wherein DNA encoding the L-pipecolic acid hydroxylase comprises the same nucleotide sequence as the nucleotide sequence represented by SEQ ID NO: 1 except that one or several bases are deleted, substituted, inserted, and/or added, which DNA encodes a protein consisting of an amino acid sequence with an identity of not less than 90% to the amino acid sequence of SEQ ID NO: 2, the protein has one or more amino acid substitution with other amino acid selected from: substitution of phenylalanine at position 5, substitution of cysteine at position 23, and substitution of aspartic acid at position 282.

4. A method of producing a hydroxy-L-pipecolic acid, the method comprising:
allowing an L-pipecolic acid hydroxylase, a microorganism or cell having the ability to produce the enzyme, a processed product of the microorganism or cell, and/or a culture liquid comprising the enzyme and obtained by culturing the microorganism or cell, to act on L-pipecolic acid as a substrate in the presence of 2-oxoglutaric acid and ferrous ion,
wherein the L-pipecolic acid hydroxylase comprises a protein consisting of an amino acid sequence with an identity of not less than 90% to the amino acid sequence of SEQ ID NO: 2, the protein has one or more amino acid substitution with other amino acid selected from: substitution of phenylalanine at position 5, substitution of cysteine at position 23, and substitution of aspartic acid at position 282.

5. The method of producing a hydroxy-L-pipecolic acid according to claim 4,
wherein the protein has one or more amino acid substitution selected from: substitution of phenylalanine with tyrosine at position 5, substitution of cysteine with alanine at position 23, and substitution of aspartic acid with glutamic acid at position 282.

6. The method of producing a hydroxy-L-pipecolic acid according to claim 4, further comprising:
allowing L-lysine and/or DL-lysine to react with
(i-1) one or more enzymes selected from the group consisting of an L-amino acid oxidase, an L-amino acid dehydrogenase and an L-amino acid aminotransferase, or
(i-2) an amino acid racemase and one or more enzymes selected from the group consisting of a D-amino acid oxidase, a D-amino acid dehydrogenase and a D-amino acid aminotransferase,
for the production of 3,4,5,6-tetrahydropyridine-2-carboxylic acid; and subsequently
allowing an N-methyl-L-amino acid dehydrogenase to act on the 3,4,5,6-tetrahydropyridine-2-carboxylic acid for the production of the L-pipecolic acid as the substrate.

7. The method of producing a hydroxy-L-pipecolic acid according to claim 4, further comprising:
allowing L-lysine to react with one or more enzymes selected from the group consisting of an L-lysine 6-oxidase, an L-lysine 6-dehydrogenase and an L-lysine 6-aminotransferase, for the production of 2,3,4,5-tetrahydropyridine-2-carboxylic acid; and subsequently
allowing a pyrroline-5-carboxylate reductase to act on the 2,3,4,5-tetrahydropyridine-2-carboxylic acid for the production of the L-pipecolic acid as the substrate.

8. The method of producing a hydroxy-L-pipecolic acid according to claim 4, further comprising allowing a lysine cyclodeaminase to act on L-lysine for the production of the L-pipecolic acid as the substrate.

9. The method of producing a hydroxy-L-pipecolic acid according to claim 4, wherein the content of L-proline in the L-pipecolic acid as the substrate is not more than 10% (w/w).

10. The method of producing a hydroxy-L-pipecolic acid according to claim 4, wherein the microorganism or cell having the ability to produce the enzyme is a microorganism or cell transformed with DNA encoding the L-pipecolic acid hydroxylase comprises DNA comprising the same nucleotide sequence as the nucleotide sequence represented by SEQ ID NO: 1 except that one or several bases are deleted, substituted, inserted, and/or added, which DNA encodes a protein consisting of an amino acid sequence with an identity of not less than 90% to the amino acid sequence of SEQ ID NO: 2, the protein has one or more amino acid substitution with other amino acid selected from: substitution of phenylalanine at position 5, substitution of cysteine at position 23, and substitution of aspartic acid at position 282.

11. A method of producing a (5S)-hydroxy-L-pipecolic acid, the method comprising:
allowing an L-pipecolic acid hydroxylase, a microorganism or cell having the ability to produce the enzyme, a processed product of the microorganism or cell, and/or a culture liquid comprising the enzyme and obtained by culturing the microorganism or cell, to act on L-pipecolic acid as a substrate in the presence of 2-oxoglutaric acid and ferrous ion,
wherein the L-pipecolic acid hydroxylase comprises a protein consisting of an amino acid sequence with an identity of not less than 90% to the amino acid sequence of SEQ ID NO: 2, the protein has one or more amino acid substitution with other amino acid selected from: substitution of phenylalanine at position 5, substitution of cysteine at position 23, and substitution of aspartic acid at position 282.

12. The method of producing a (5S)-hydroxy-L-pipecolic acid according to claim 11, wherein the protein has one or more amino acid substitution selected from: substitution of phenylalanine with tyrosine at position 5, substitution of cysteine with alanine at position 23, and substitution of aspartic acid with glutamic acid at position 282.

* * * * *